US012588870B2

(12) United States Patent　　(10) Patent No.: US 12,588,870 B2
Vaidyanathan　　(45) Date of Patent: Mar. 31, 2026

(54) ELECTRODE ORIENTATION DETECTION

(71) Applicant: Medtronic, Inc., Minneapolis, MN (US)

(72) Inventor: Janardan Vaidyanathan, Thane (IN)

(73) Assignee: Medtronic, Inc., Minneapolis, MN (US)

( * ) Notice: Subject to any disclaimer, the term of this patent is extended or adjusted under 35 U.S.C. 154(b) by 298 days.

(21) Appl. No.: 18/317,735

(22) Filed: May 15, 2023

(65) Prior Publication Data

US 2023/0363709 A1　　Nov. 16, 2023

Related U.S. Application Data

(60) Provisional application No. 63/364,784, filed on May 16, 2022.

(51) Int. Cl.
*A61B 5/00*　　(2006.01)
*A61B 5/01*　　(2006.01)
*A61B 5/055*　　(2006.01)
*G01R 33/48*　　(2006.01)

(52) U.S. Cl.
CPC .......... *A61B 5/4887* (2013.01); *A61B 5/0042* (2013.01); *A61B 5/01* (2013.01); *A61B 5/055* (2013.01); *G01R 33/4806* (2013.01)

(58) Field of Classification Search
CPC .................................................. A61B 5/4887
See application file for complete search history.

(56) References Cited

U.S. PATENT DOCUMENTS

| | | | |
|---|---|---|---|
| 8,995,731 B2 | 3/2015 | Joglekar | |
| 10,088,537 B2 | 10/2018 | Pendse et al. | |
| 10,265,531 B2 | 4/2019 | Bokil | |
| 10,335,590 B2 | 7/2019 | Katnani et al. | |
| 10,537,277 B2 | 1/2020 | Wu et al. | |
| 10,631,937 B2 | 4/2020 | Tyulmankov et al. | |
| 2016/0144167 A1* | 5/2016 | Bakker | A61B 5/06 607/63 |
| 2016/0331960 A1* | 11/2016 | Katnani | A61N 1/0534 |
| 2018/0104482 A1 | 4/2018 | Bokil | |
| 2019/0059773 A1 | 2/2019 | Laughlin et al. | |
| 2020/0029894 A1 | 1/2020 | Gerber et al. | |
| 2020/0237326 A1 | 7/2020 | Achatz et al. | |

(Continued)

OTHER PUBLICATIONS

Elwassif et al., "Bio-beat transfer model of deep brain stimulation-induced temperature changes", Journal of Neural Engineering, vol. 3, Institute of Physics Publishing, Nov. 6, 2006, pp. 306-315, doi:10.1088/1741-2560/3/4/008.

(Continued)

*Primary Examiner* — Joseph M Santos Rodriguez
(74) *Attorney, Agent, or Firm* — Shumaker & Sieffert, P.A.

(57) ABSTRACT

Devices, systems, and techniques are disclosed for determining an orientation of electrodes within a patient. For example, method may include receiving magnetic resonance imaging (MRI) data of tissue of a patient that received electrical stimulation via at least one electrode disposed in the patient, generating, based on the MRI data, stimulation temperature data representative of temperature changes in the tissue of the patient during the electrical stimulation, and determining, based on the temperature data, an orientation of the at least one electrode with respect to the tissue of the patient.

20 Claims, 9 Drawing Sheets

(56)           References Cited

U.S. PATENT DOCUMENTS

2020/0268434 A1     8/2020   Drown et al.
2020/0337636 A1    10/2020   Souza et al.

OTHER PUBLICATIONS

Madore et al., "Chapter 34: MR Thermometry", Advances in
Magnetic Resonance Technology and Applications, vol. 1, Brigham
and Women's Hospital, Harvard Medical School, Advanced Lab for
MRI and Acoustics, Boston, MA, USA, Dec. 7, 2020, pp. 885-905,
https://doi.org/10.1016/B978-0-12-817057-1.00036-6.

* cited by examiner

104

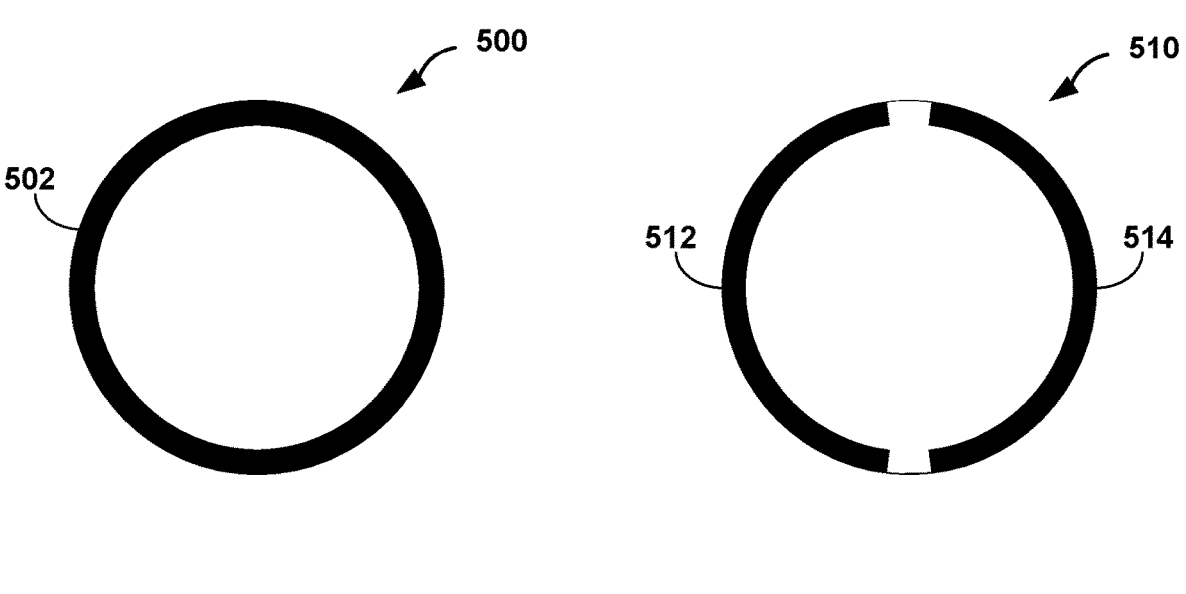
FIG. 5A                    FIG. 5B
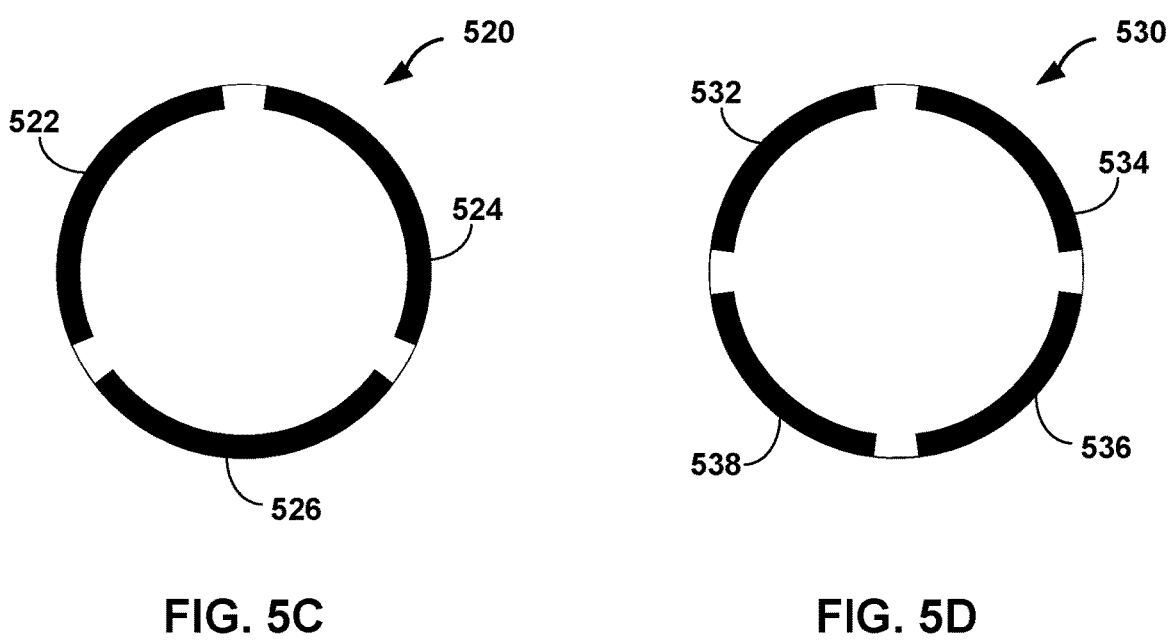
FIG. 5C                    FIG. 5D

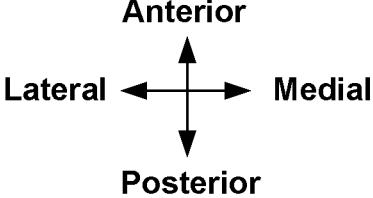
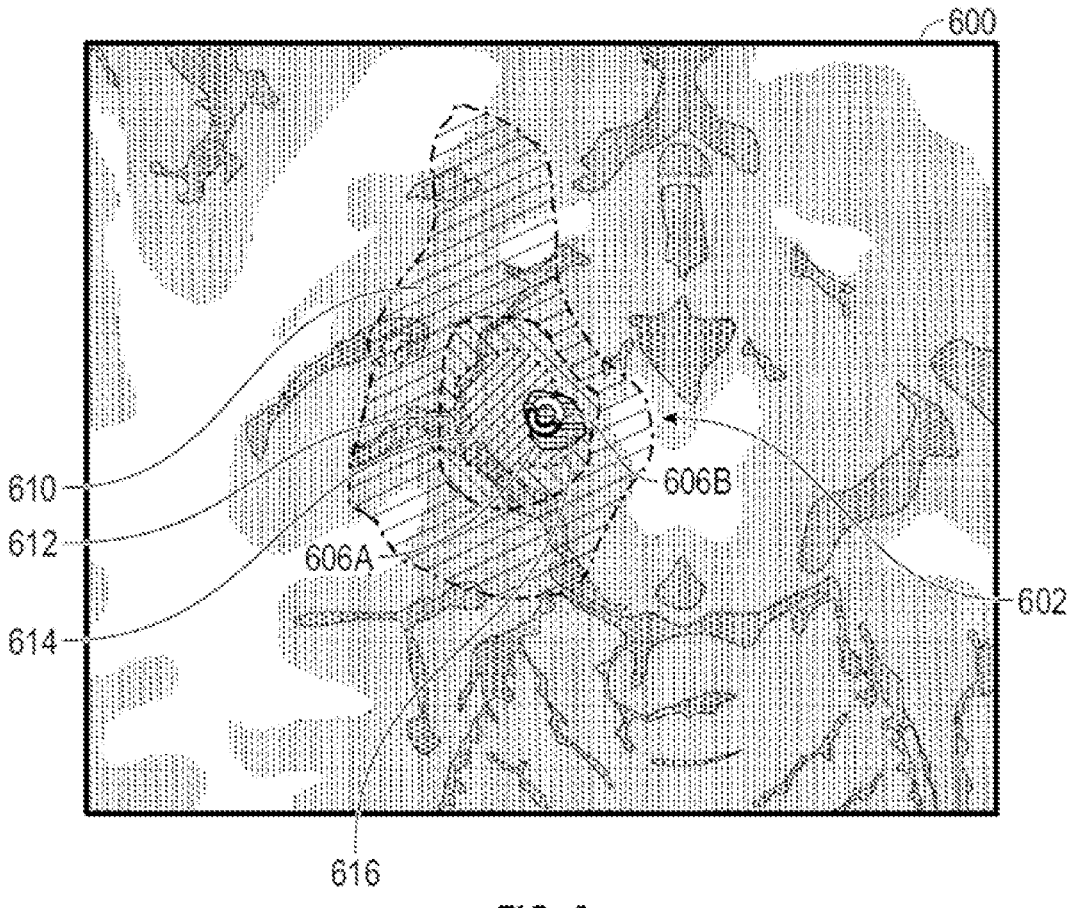
FIG. 6

800 — RECEIVE BASELINE MRI DATA PRIOR TO STIMULATION

802 — DELIVER STIMULATION TO AT LEAST ONE ELECTRODE AND RECEIVE STIMULATION MRI DATA GENERATED AFTER STIMULATION

804 — GENERATE STIMULATATION TEMPERATURE DATA BASED ON STIMULATION MRI DATA

806 — COMPARE BASELINE TEMPERATURE DATA AND STIMULATION TEMPERATURE DATA

808 — DETERMINE ORIENTATION OF ELECTRODE

ELECTRODE ORIENTATION DETECTION

This application claims the benefit of U.S. Provisional Patent Application No. 63/364,784, filed May 16, 2022, the entire contents of which is incorporated herein by reference.

TECHNICAL FIELD

This disclosure generally relates to electrical stimulation, and identifying orientation of electrodes.

BACKGROUND

Medical devices may be external or implanted, and may be used to deliver electrical stimulation therapy to various tissue sites of a patient to treat a variety of symptoms or conditions such as chronic pain, tremor, Parkinson's disease, dystonia, other movement disorders, epilepsy, headache, psychiatric disorders, memory dysfunction, urinary or fecal incontinence, sexual dysfunction, obesity and eating disorders, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Hence, electrical stimulation may be used in different therapeutic applications, such as deep brain stimulation (DBS), occipital nerve stimulation (ONS), spinal cord stimulation (SCS), pelvic stimulation, sacral nerve stimulation, phrenic nerve stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes for delivery of the stimulation, a waveform pattern, a polarity of each selected electrode, a voltage or current amplitude, a pulse width, and a pulse frequency as stimulation parameters in a multitude of modes continuous/cycling and configurations. A set of parameters, such as a set including electrode combination and/or configuration, electrode polarity, voltage or current amplitude, pulse width and pulse rate, may be referred to as a program in the sense that they define the electrical stimulation therapy to be delivered to the patient. Several programs could be assimilated into one or more groups.

SUMMARY

In general, the disclosure describes devices, systems, and techniques for determining orientation of electrodes with respect to tissue (e.g., with respect to patient specific anatomy). For example, a system may receive magnetic resonance imaging (MRI) data of patient anatomy (e.g., a patient specific atlas from a target specific radiological sequence), where the MRI data corresponds to delivery of electrical stimulation via at least one electrode disposed in tissue of a patient. Based on the MRI data, the system may generate temperature data, where the temperature data may represent temperature changes in tissue of the patient during stimulation. The system may then determine an orientation of the electrode with respect of the tissue, such as the brain, based on the temperature data.

In an example, a lead may carry electrodes disposed at different positions around a perimeter or shaft of the lead. The system may sense a baseline temperature in tissue, for example, using MRI data generated prior to stimulation. The system, or other device, may deliver stimulation to the patient via the electrodes, and the system can sense a subsequent temperature in tissue for the electrodes and based on subsequent MRI data generated during and/or after stimulation is delivered. The system may then compare the baseline temperature with the subsequent temperature to determine orientation of the electrodes. For example, the system may correlate the locations of change in temperature on the MRI data to the locations of respective electrodes carried by the lead.

In one example, a method includes receiving, by a processing circuitry, magnetic resonance imaging (MRI) data of tissue of a patient that received electrical stimulation via at least one electrode disposed in the patient, generating, based on the MRI data, stimulation temperature data representative of temperature changes in the tissue of the patient during the electrical stimulation, and determining, by the processing circuitry and based on the temperature data, an orientation of the at least one electrode with respect to the tissue of the patient.

In another example, a system includes processing circuitry configured to receive magnetic resonance imaging (MRI) data of tissue of a patient that received electrical stimulation via at least one electrode of a plurality of electrodes disposed in the patient, generate, based on the MRI data, stimulation temperature representative of temperature changes in tissue of the patient during electrical stimulation, determine, by the processing circuitry and based on the temperature data, an orientation of the at least one electrode with respect to the tissue of the patient.

In another example, a computer-readable storage medium including instructions that, when executed, cause processing circuitry to receive MRI data of tissue of a patient that received electrical stimulation via at least one electrode disposed in the patient, generate, based on the MRI data, stimulation temperature data representative of temperature changes in tissue of the patient during stimulation, and determine, by the processing circuitry and based on the temperature data, an orientation of the at least one electrode with respect to the tissue of the patient.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

FIGS. 5A, 5B, 5C, and 5D are conceptual diagrams of example electrodes disposed around a perimeter of a lead at a particular longitudinal location.

FIG. 6 is a baseline temperature map of tissue with a lead placed within tissue.

DETAILED DESCRIPTION

Figure 1:
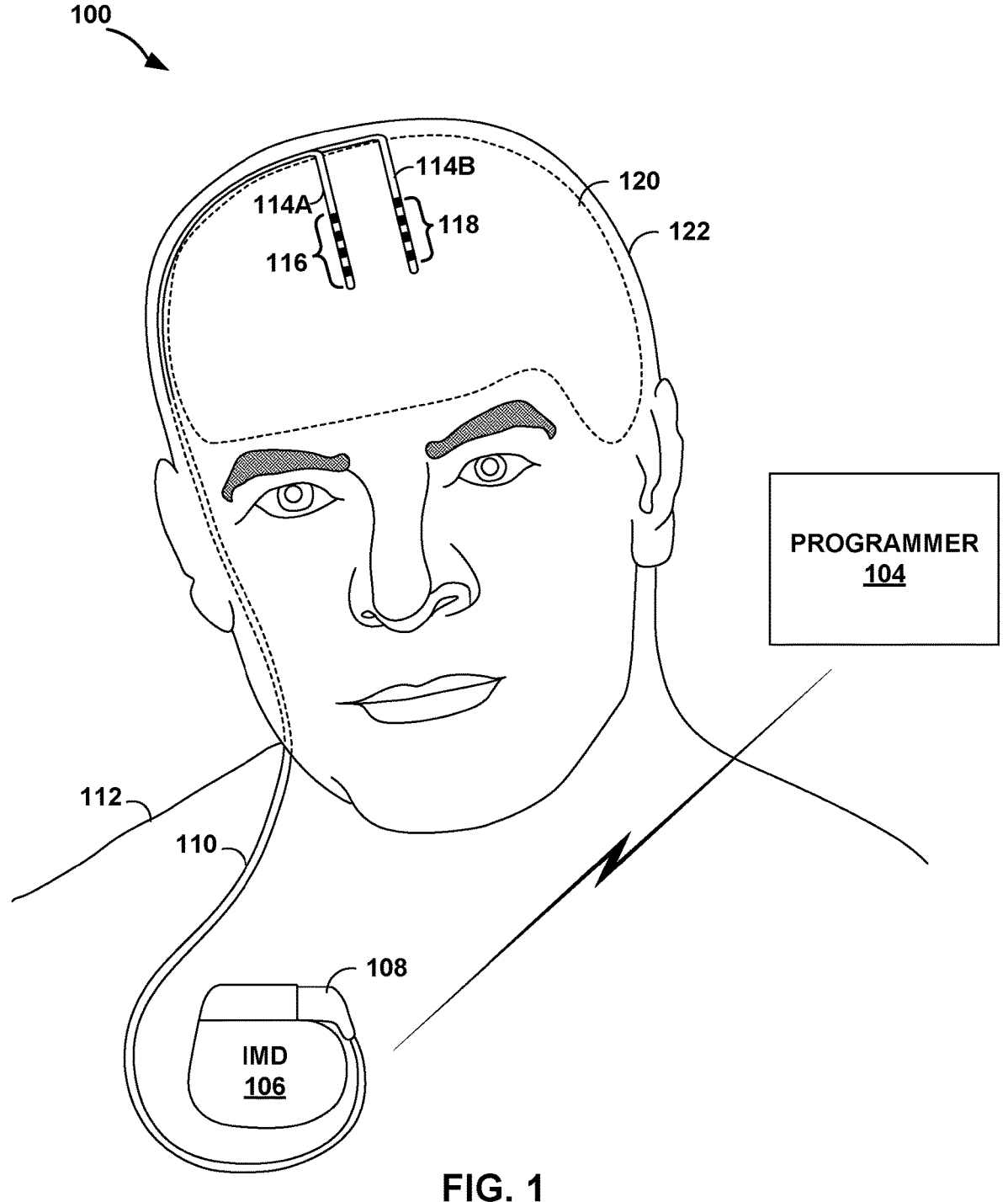
FIG. 1 is a conceptual diagram illustrating an example system that includes an implantable medical device (IMD) configured to deliver DB S to a patient according to an example of the techniques of the disclosure.

This disclosure describes various devices, systems, and techniques for determining orientation of electrodes within a patient. A patient may suffer from one or more symptoms treatable by electrical stimulation therapy. For example, a patient may suffer from brain disorder such as Parkinson's disease, Alzheimer's disease, another type of movement disorder, neurological or psychiatric condition. Deep brain stimulation (DBS) may be an effective treatment to reduce the symptoms associated with such disorders. However, efficacy of stimulation therapy may be reliant on selecting appropriate electrodes and other stimulation parameter values that direct an electric field to a target region of tissue. Stimulation of tissue outside of the target region may elicit undesirable effects and/or reduce the efficacy of the therapy. In addition, a lead, and the electrodes it carries, may move within tissue after implantation. Therefore, if a lead rotates about a longitudinal axis and/or shifts longitudinally within tissue after stimulation parameters are determined, the stimulation therapy may be less effective and/or the stimulation may result in undesirable side effects for the patient. Post implant, it is helpful to determine orientation of the electrodes, for example, for a DBS lead. However, some systems, such as a magnetic resonance imaging (MRI) system may obscure visibility of the electrode orientation due to the artifact caused by the metallic electrodes of the lead or other metallic components.

The systems and techniques herein are directed to using MRI scans (e.g., conditionally safe target specific sequences to create a patient specific atlas) to identify anatomy of the patient structure and orientation of electrode segments, for example orientation of electrode segments on a directional or segmented lead that facilitates fragmentation/fractionalization of stimulation energy. In some examples, a controlled amount of electrical stimulation may be applied to a particular electrode segment, and the controlled amount of electrical stimulation to the electrode segment may induce temperature changes in surrounding tissue. For example, some electrical stimulation protocols may increase the temperature of surrounding tissue by up to 0.8 degrees Centigrade. The systems and techniques may generate one or more temperature maps, for example using MR thermometry, where MR thermometry is the measurement of absolute temperature or relative temperature changes by comparing the acquired data to reference data at a known temperature using MRI. MR thermometry uses a change in Larmor frequency of MR signals to determine temperature changes, since when tissue temperature changes, the Larmor frequency also changes. The inferred temperature value may be based on a temperature map (T-map) derived from proton resonance frequency shift MR imaging. For example, the temperature fields can be obtained by phase shift which is measuring the phase difference due to the resonance frequency variation occurring when the temperature is modified from a known baseline reference phase.

In some examples, temperature maps may be generated during or after application of the electrical stimulation. In some examples, a baseline reference temperature map may be generated prior to application of the electrical stimulation, and a subsequent temperature map may be generated during or after application of the electrical stimulation. Using the one or more temperature maps, the system may determine the change in temperature around the stimulated electrode segment, and determine the orientation of the electrode based on the temperature changes from the baseline reference temperature map. In some examples, the subsequent temperature map may be compared to a baseline reference temperature map to determine the orientation of the electrode based on the temperature changes shown in the temperature maps.

Although this disclosure is directed to DBS therapy, the systems, devices, and techniques described herein may similarly detect movement of leads and electrodes and/or their orientation implanted outside of the brain, such as near other nerves or muscles for different diagnostic or therapeutic applications, such as spinal cord stimulation (SCS), occipital nerve stimulation, pelvic stimulation, sacral nerve stimulation, phrenic nerve stimulation, gastric stimulation, or peripheral nerve field stimulation (PNFS). Moreover, a human patient is described for example purposes herein, but similar systems, devices, and techniques may be used for other animals in other examples.

FIG. 1 is a conceptual diagram illustrating an example system 100 that includes an implantable medical device (IMD) 106 configured to deliver DBS to patient 112 according to an example of the techniques of the disclosure. As shown in the example of FIG. 1, example system 100 includes medical device programmer 104, implantable medical device (IMD) 106, lead extension 110, and leads 114A and 114B with respective sets of electrodes 116, 118. In the example shown in FIG. 1, electrodes 116, 118 of leads 114A, 114B are positioned to deliver electrical stimulation to a tissue site within brain 120, such as a deep brain site under the dura mater of brain 120 of patient 112. In some examples, delivery of stimulation to one or more regions of brain 120, such as the subthalamic nucleus, globus pallidus or thalamus, may be an effective treatment to manage movement disorders, such as Parkinson's disease. Some or all of electrodes 116, 118 also may be positioned to sense or record neurological brain signals within brain 120 of patient 112. In some examples, some of electrodes 116, 118 may be configured to sense or record neurological brain signals and others of electrodes 116, 118 may be configured to deliver adaptive electrical stimulation to brain 120. In other examples, all of electrodes 116, 118 are configured to both sense or record neurological brain signals and deliver adaptive electrical stimulation to brain 120.

IMD 106 includes a therapy module (e.g., which may include processing circuitry, signal generation circuitry or other electrical circuitry configured to perform the functions attributed to IMD 106) that includes a stimulation generator configured to generate and deliver electrical stimulation therapy to patient 112 via a subset of electrodes 116, 118 of leads 114A and 114B, respectively. The subset of electrodes 116, 118 that are used to deliver electrical stimulation to patient 112, and, in some cases, the polarity of the subset of electrodes 116, 118, may be referred to as a stimulation electrode combination or configuration. The group of electrodes 116, 118 includes at least one electrode and can include a plurality of electrodes. In some examples, the plurality of electrodes 116 and/or 118 may have a complex electrode geometry such that two or more electrodes of the lead are located at different positions around the perimeter of the respective lead (e.g., different positions around a longitudinal axis or shaft of the lead). In some examples, at least one electrode includes at least two electrodes disposed at different axial positions along the lead in the patient. In some examples, at least one electrode includes at least two electrodes disposed at different axial positions along the lead, and may be disposed at a same or different circumferential position around a perimeter of the lead.

In some examples, the neurological signals (e.g., an example type of electrical signals) sensed or recorded within brain 120 may reflect changes in electrical current produced by the sum of electrical potential differences across brain tissue. Examples of neurological brain signals include, but are not limited to, electrical signals generated from local field potentials (LFP) sensed within one or more regions of brain 120, such as an electroencephalogram (EEG) signal, or an electrocorticogram (ECoG) signal. Local field potentials, however, may include a broader genus of electrical signals within brain 120 of patient 112 (e.g., which signify brain state, disease state or symptom state).

In some examples, the neurological brain signals that are used to select a stimulation electrode combination may be sensed within the same region of brain 120 as the target tissue site for the electrical stimulation. As previously indicated, these tissue sites may include tissue sites within anatomical structures such as the thalamus, subthalamic nucleus or globus pallidus of brain 120, as well as other target tissue sites. The specific target tissue sites and/or regions within brain 120 may be selected based on the patient condition. Thus, due to these differences in target locations, in some examples, the electrodes used for delivering electrical stimulation may be different than the electrodes used for sensing neurological brain signals. In other examples, the same electrodes may be used to deliver electrical stimulation and sense brain signals. However, this configuration would require the system to switch between stimulation generation and sensing circuitry and may reduce the time the system can sense brain signals.

Electrical stimulation generated by IMD 106 may be configured to manage a variety of disorders and conditions. In some examples, the stimulation generator of IMD 106 is configured to generate and deliver electrical stimulation pulses to patient 112 via electrodes of a selected stimulation electrode combination. However, in other examples, the stimulation generator of IMD 106 may be configured to generate and deliver a continuous wave signal, e.g., a sine wave or triangle wave. In either case, a stimulation generator within IMD 106 may generate the electrical stimulation therapy for DBS according to a therapy program that is selected at that given time in therapy. In examples in which IMD 106 delivers electrical stimulation in the form of stimulation pulses, a therapy program may include a set of therapy parameter values (e.g., stimulation parameters), such as a stimulation electrode combination for delivering stimulation to patient 112, waveform pattern, pulse frequency, pulse width, and a current or voltage amplitude of the pulses. As previously indicated, the electrode combination may indicate the specific electrodes 116, 118 that are selected to deliver stimulation signals to tissue of patient 112 and the respective polarities of the selected electrodes. IMD 106 may deliver electrical stimulation intended to contribute to a therapeutic effect. In some examples, IMD 106 may also, or alternatively, deliver electrical stimulation intended to be sensed or recorded by other electrode and/or elicit a physiological response, such as an evoked compound action potential (ECAP) or resonant response, that can be sensed or recorded by electrodes.

IMD 106 may be implanted within a subcutaneous pocket below the clavicle, or, alternatively, on or within cranium 122 or at any other suitable site within patient 112. Generally, IMD 106 is constructed of a biocompatible material that resists corrosion and degradation from body fluids. IMD 106 may comprise a hermetic housing to substantially enclose components, such as a processor, therapy module, and memory.

As shown in FIG. 1, implanted lead extension 110 is coupled to IMD 106 via connector 108 (also referred to as a connector block or a header of IMD 106). In the example of FIG. 1, lead extension 110 traverses from the implant site of IMD 106 and along the neck of patient 112 to cranium 122 of patient 112 to access brain 120. In the example shown in FIG. 1, leads 114A and 114B (collectively "leads 114") are implanted within the right and left hemispheres, respectively, of patient 112 in order deliver electrical stimulation to and/or sense or record from one or more regions of brain 120, which may be selected based on the patient condition or disorder controlled by therapy system 100. The specific target tissue site and the stimulation electrodes used to deliver stimulation to the target tissue site, however, may be selected, e.g., according to the identified patient behaviors associated with one or more brain disorders and/or other sensed patient signals. Other lead 114 and IMD 106 implant sites are contemplated. For example, IMD 106 may be implanted on or within cranium 122, in some examples. Or leads 114 may be implanted within the same hemisphere or IMD 106 may be coupled to a single lead implanted in a single hemisphere. Although leads 114 may have ring or omnidirectional electrodes at different longitudinal positions as shown in FIG. 1, leads 114 may have electrodes disposed at different positions around the perimeter of the lead (e.g., different circumferential positions for a cylindrical shaped lead in a low resolution or high resolution segmented directional configuration for fractionalization of stimulation) as shown in the examples of FIGS. 4A, 4B, 5A, 5B, 5C, and 5D.

Leads 114 illustrate an example lead set that include axial leads carrying ring or omnidirectional electrodes disposed at different axial positions (or longitudinal positions). In other examples, leads may be referred to as "paddle" leads carrying planar arrays of electrodes on one side of the lead structure. In addition, as described herein, complex lead array geometries may be used in which electrodes are disposed at different respective longitudinal positions and different positions around the perimeter of the lead. As described herein, IMD 106 may be configured to detect movement of the lead with respect to tissue when monitoring electrical signals sensed by the different electrodes between different times.

Although leads 114 are shown in FIG. 1 as being coupled to a common lead extension 110, in other examples, leads 114 may be coupled to IMD 106 via separate lead extensions or directly to connector 108. Leads 114 may be positioned to deliver electrical stimulation to and/or sense or record from one or more target tissue sites within brain 120 to manage patient symptoms associated with a disorder such as a movement disorder of patient 112. Leads 114 may be implanted to position electrodes 116, 118 at desired locations of brain 120 through respective burr holes in cranium 122. Leads 114 may be placed at any location within brain 120 such that electrodes 116, 118 are capable of providing electrical stimulation to and/or sense or record from target tissue sites within brain 120 during treatment. For example, electrodes 116, 118 may be surgically implanted under the dura mater of brain 120 or within the cerebral cortex of brain 120 via a burr hole in cranium 122 of patient 112, and electrically coupled to IMD 106 via one or more leads 114.

In the example shown in FIG. 1, electrodes 116, 118 of leads 114 are shown as ring electrodes. Ring electrodes (annular having cylindrical symmetric design) may be used in DBS applications because they are relatively simple to program and are capable of delivering an omnidirectional electrical field to any tissue adjacent to electrodes 116, 118. In other examples, electrodes 116, 118 may have different configurations. For example, in some examples, at least some of the electrodes 116, 118 of leads 114 may have a complex electrode array geometry that is capable of producing shaped electrical fields. The complex electrode array geometry may include multiple electrodes (e.g., partial ring or segmented electrodes) around the outer perimeter of each lead 114, rather than one ring electrode, such as the examples shown in FIGS. 4A and 4B. In this manner, electrical stimulation may be fractionalized and directed in a specific direction from leads 114 to enhance therapy efficacy and reduce possible adverse side effects from stimulating a large volume of tissue and/or sense or record from target tissue. In some examples, a housing of IMD 106 may include one or more stimulation and/or sensing electrodes. In alternative examples, leads 114 may have shapes other than elongated cylinders as shown in FIG. 1. For example, leads 114 may be paddle leads, spherical leads, bendable leads, or any other type of shape effective in treating patient 112 and/or minimizing invasiveness of leads 114.

In the example shown in FIG. 1, IMD 106 includes a memory to store a plurality of therapy programs that each define a set of therapy parameter values. In some examples, IMD 106 may select a therapy program from the memory based on various parameters, such as sensed patient signals and the identified patient behaviors e.g., as patient behaviors associated with one or more brain disorders, and/or other sensed patient signals. IMD 106 may generate electrical stimulation based on the selected therapy program to manage the patient symptoms associated with a movement disorder.

External programmer 104 wirelessly communicates with IMD 106 as needed to provide or retrieve therapy information. Programmer 104 is an external computing device that the user, e.g., a clinician and/or patient 112, may use to communicate with IMD 106. For example, programmer 104 may be a clinician programmer that the clinician uses to communicate with IMD 106 and program one or more therapy programs for IMD 106. Alternatively, programmer 104 may be a patient programmer that allows patient 112 to select programs or groups and/or view and modify allowable therapy parameters within a preset range in addition to triggering capture of a tagged/untagged sensing event. The clinician programmer may include more programming features than the patient programmer. In other words, more complex or sensitive tasks may only be allowed by the clinician programmer to prevent an untrained patient from making undesirable changes to IMD 106. IMD 106 may also transmit notifications to programmer 104 for delivery to a user in response to detecting that one of leads 114 has moved with respect to tissue. Programmer 104 may enter a new programming session for the user to select new stimulation parameters for subsequent therapy.

When programmer 104 is configured for use by the clinician, programmer 104 may be used to transmit initial programming information to IMD 106. This initial information may include hardware information, such as the type of leads 114 and the electrode arrangement, the position of leads 114 within brain 120, the configuration of electrode array 116, 118, initial programs defining therapy parameter values, a known electrode orientation from a previous session if available and any other information the clinician desires to program into IMD 106. Programmer 104 may also be capable of completing functional tests (e.g., measuring the impedance of electrodes 116, 118 of leads 114). In some examples, programmer 104 may receive sensed signals or representative information and perform the same techniques and functions attributed to IMD 106 herein. In other examples, a remote server (e.g., a standalone server or part of a cloud service) may perform the functions attributed to IMD 106, programmer 104, or any other devices described herein.

The clinician may also store therapy programs within IMD 106 with the aid of programmer 104. During a programming session, the clinician may determine one or more therapy programs that may provide efficacious therapy to patient 112 to address symptoms associated with the patient condition, and, in some cases, specific to one or more different patient states, such as a sleep state, movement state or rest state. For example, the clinician may select one or more stimulation electrode combination with which stimulation is delivered to brain 120. During the programming session, the clinician may evaluate the efficacy of the specific program being evaluated based on feedback provided by patient 112 or based on one or more physiological parameters of patient 112 (e.g., muscle activity, muscle tone, rigidity, tremor, etc.) and/or sensed or recorded signals. Alternatively, identified patient behavior from video information may be used as feedback during the initial and subsequent programming sessions. Programmer 104 may assist the clinician in the creation/identification of therapy programs by providing a methodical system for identifying potentially beneficial therapy parameter values.

Programmer 104 may also be configured for use by patient 112. When configured as a patient programmer, programmer 104 may have limited functionality (compared to a clinician programmer) in order to prevent patient 112 from altering critical functions of IMD 106 or applications that may be detrimental to patient 112. In this manner, programmer 104 may only allow patient 112 to adjust values for certain therapy parameters or set an available range of values for a particular therapy parameter and/or triggering capture of a sensing event.

Programmer 104 may also provide an indication to patient 112 when therapy is being delivered, when patient input has triggered a change in therapy or when the power source within programmer 104 or IMD 106 needs to be replaced or recharged. For example, programmer 104 may include an alert LED, may flash a message to patient 112 via a programmer display, generate an audible sound or somatosensory cue to confirm patient input was received, e.g., to indicate a patient state or to manually modify a therapy parameter. Programmer 104, such as the patient programmer, may be used to trigger sensing/recording of events through physician configured electrodes for varying lengths of time.

Therapy system 100 may be implemented to provide chronic stimulation therapy to and/or sense or record from patient 112 over the course of several months or years. However, system 100 may also be employed on a trial basis to evaluate therapy before committing to full implantation. If implemented temporarily, some components of system 100 may not be implanted within patient 112. For example, patient 112 may be fitted with an external medical device, such as a trial stimulator, rather than IMD 106. The external medical device may be coupled to percutaneous leads or to implanted leads via a percutaneous extension. If the trial stimulator indicates DBS system 100 provides effective treatment to patient 112, the clinician may implant a chronic stimulator within patient 112 for relatively long-term treatment.

Although IMD 106 is described as delivering electrical stimulation therapy to brain 120, IMD 106 may be configured to direct electrical stimulation to other anatomical regions of patient 112 in other examples. In other examples, system 100 may include an implantable drug pump in addition to, or in place of, IMD 106. Further, an IMD may provide other electrical stimulation such as spinal cord stimulation to treat a movement disorder.

According to the techniques of the disclosure, system 100 may determine orientation of one or more electrodes, such as electrode segments disposed at different positions around a perimeter of a lead, for example using MRI data. This determination of electrode orientation may be performed after implantation and prior to deliver of therapy. In some examples, system 100 may determine whether a lead has shifted, displaced, migrated, or moved, with respect to the tissue within which the lead is implanted. IMD 106, programmer 104, a different external device, or any combination thereof, may determine the orientation of one or more electrodes disposed in patient 112 based on MRI data as described herein. For example, IMD 106 may receive MRI data indicative of temperature data representative of temperature changes in tissue while electrical stimulation is provided by the at least one electrode. IMD 106 may include a memory configured to store this received MRI data. In some examples, the memory may be configured to store MRI data and sensed signals of the patient. In some examples, the memory may be configured to store a temperature data representative of temperature changes or normal/existing temperature in the tissue, based on MRI data, for example with and without electrical stimulation.

In some examples, sensing circuitry within IMD 106 may sense the potential difference between respective electrode combinations. The electrode combinations may include only two or more electrodes on the same lead (e.g., bipolar sensing). In this manner, the first electrical signals and the second electrical signals may include differential signals between respective electrode combinations of the plurality of electrode combinations. In other examples, an electrode combination may include at least one electrode from two different leads and/or between hemispheres (which may be referred to as split sensing, for example). In another example, the electrical signals may be sensed via unipolar sensing where each electrode combination includes one electrode from a lead and an indifferent electrode (e.g., an electrode or conductive surface on IMD 106 housing or set at some distance away from the lead) that is relatively far from the electrode. In this manner, the electrical signals may include monopolar signals between respective electrode combinations of the plurality of electrode combinations. In one example, each electrode combination includes an electrode carried by a lead, where the lead defines a longitudinal axis and includes a plurality of electrodes disposed at different positions around the longitudinal axis of the lead (e.g., leads 400 and 410 of FIGS. 4A and 4B).

System 100 (e.g., IMD 106) may also include processing circuitry configured to receive signal information indicative of second electrical signals sensed from the plurality of electrode combinations at a second time after the first time. The processing circuitry or sensing circuitry may generate the signal information based on the sensing circuitry sensing potential differences for each electrode combination. IMD 106 may then determine, based on the signal information, that the lead has rotated with respect to tissue and then output an indication that the lead has rotated with respect to the tissue. IMD 106 may also determine based on signal information, that the lead has deviated, migrated, displaced or re-oriented related to tissue.

In general, IMD 106 (or another device, such as programmer 104) may determine an electrode orientation or that the lead has moved with respect to tissue when the MRI data is used to generate stimulation induced temperature change data, and the stimulation induced temperature change data is different than baseline temperature data or an initial set of mapped temperature data. For example, a difference in baseline temperature data and stimulation induced temperature data may indicate an electrode orientation. Since electrical current delivered to tissue by an electrode can increase the temperature of the tissue, the increase tissue temperature indicated by the MRI data (e.g. detectable by changes in proton resonance frequency as in a T-map) can correspond to specific electrode locations within the tissue. In some examples, a difference from a first set of temperature data to a second set of temperature data may indicate an electrode has moved with respect to patient tissue.

The architecture of system 100 illustrated in FIG. 1 is shown as an example. The techniques as set forth in this disclosure may be implemented in the example system 100 of FIG. 1, as well as other types of systems not described specifically herein. Nothing in this disclosure should be construed so as to limit the techniques of this disclosure to the example architecture illustrated by FIG. 1.

Figure 2:
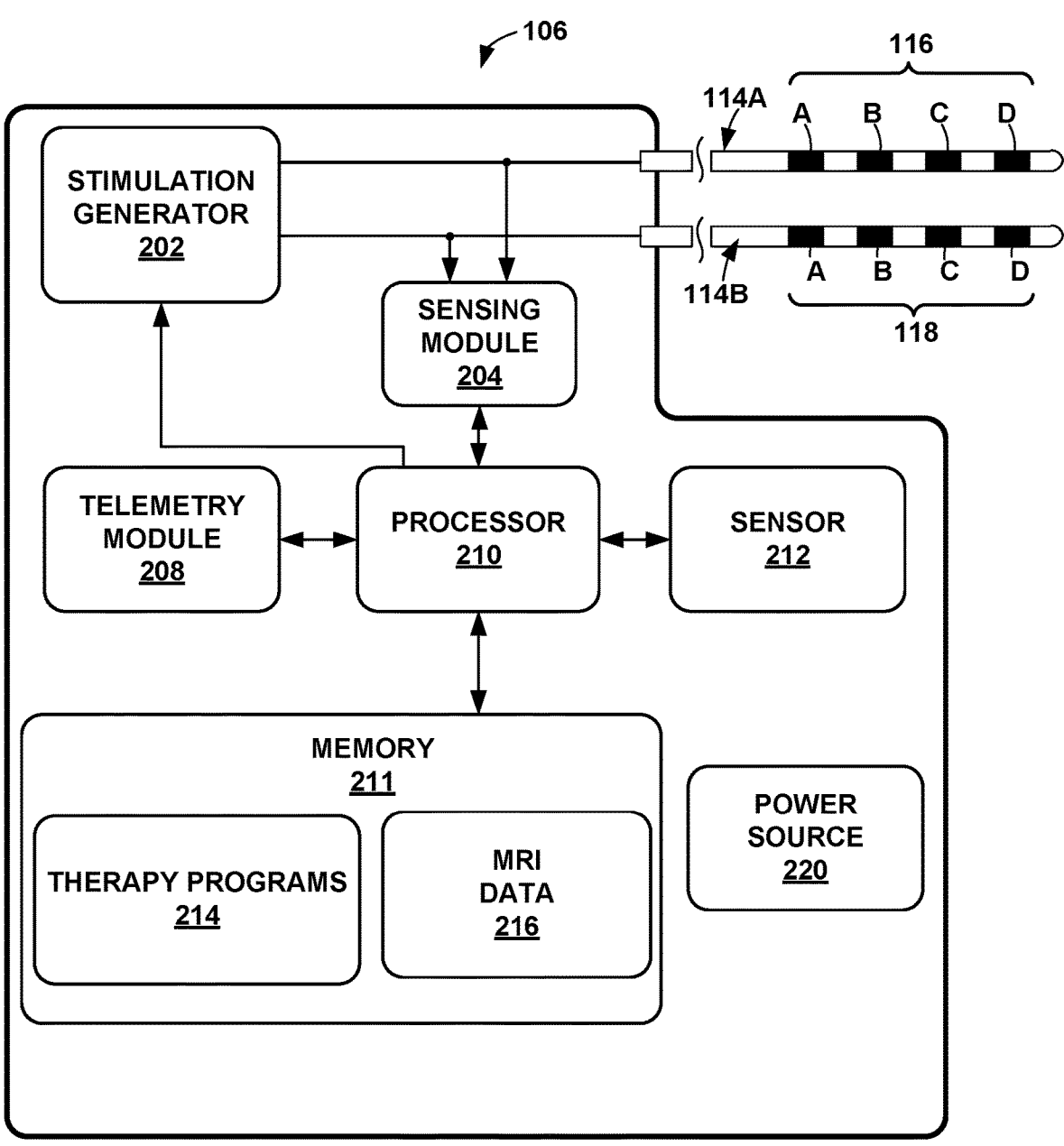
FIG. 2 is a block diagram of the example IMD of FIG. 1 for delivering DBS therapy according to an example of the techniques of the disclosure.

FIG. 2 is a block diagram of the example IMD 106 of FIG. 1 for delivering DBS therapy. In the example shown in FIG. 2, IMD 106 includes processor 210, memory 211, stimulation generator 202, sensing module 204, telemetry module 208, sensor 212, and power source 220. Each of these modules may be or include electrical circuitry configured to perform the functions attributed to each respective module. For example, processor 210 may include processing circuitry, sensing module 204 may include sensing circuitry, and telemetry module 208 may include telemetry circuitry. Memory 211 may include any volatile or non-volatile media, such as a random-access memory (RAM), read only memory (ROM), non-volatile RAM (NVRAM), electrically erasable programmable ROM (EEPROM), flash memory, and the like. Memory 211 may store computer-readable instructions that, when executed by processor 210, cause IMD 106 to perform various functions. Memory 211 may be a storage device or other non-transitory medium.

In the example shown in FIG. 2, memory 211 stores therapy programs 214 that include respective stimulation parameter sets that define therapy. Each stored therapy program 214 defines a particular set of electrical stimulation parameters (e.g., a therapy parameter set), such as a stimulation electrode combination, electrode polarity, waveform pattern, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

In some examples, the sense and stimulation electrode combinations may include the same subset of electrodes 116, 118, a housing of IMD 106 functioning as an electrode, or may include different subsets or combinations of such electrodes. Thus, memory 211 can store a plurality of sense electrode combinations and, for each sense electrode combination, store information identifying the stimulation electrode combination that is associated with the respective sense electrode combination or vice versa. The associations between sense and stimulation electrode combinations can be determined, e.g., by a clinician or automatically by processor 210. In some examples, corresponding sense and stimulation electrode combinations may comprise some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy. In some examples, as discussed above, stimulation may be delivered via a stimulation electrode combination to a tissue site that is different than the tissue site closest to the corresponding sense electrode combination but is within the same region, e.g., the thalamus, of brain 120 in order to mitigate any irregular oscillations or other irregular brain activity within the tissue site associated with the sense electrode combination. In other examples, the electrodes that deliver stimulation may be carried by a lead implanted in a different region of the brain than a different lead that carries the sensing electrodes.

IMD 106 may include a memory 211 configured to store MRI data 216 indicative of temperature data representative of temperature changes in tissue while electrical stimulation is provided by at least one electrode. In some examples, memory 211 may be configured to store a known parameter set for the temperature data, and/or when a known parameter set is applied. In some examples, the memory 211 may be configured to store MRI data 216 and sensed signals of the patient. In some examples, the memory 211 may be configured to store a temperature data representative of normal temperature in the tissue, based on MRI data without stimulation to the patient.

Stimulation generator 202, under the control of processor 210, generates stimulation signals for delivery to patient 112 via selected combinations of electrodes 116, 118. An example range of electrical stimulation parameters believed to be effective in DBS to manage a movement disorder of patient may include:

1. Pulse Rate, i.e., Frequency: between approximately 0.1 Hertz and approximately 500 Hertz, such as between approximately 0.1 to 10 Hertz, approximately 40 to 185 Hertz, or such as approximately 140 Hertz.
2. In the case of a voltage controlled system, Voltage Amplitude: between approximately 0.1 volts and approximately 50 volts, such as between approximately 2 volts and approximately 3 volts.
3. In the alternative case of a current controlled system, Current Amplitude: between approximately 0.2 milliamps to approximately 100 milliamps, such as between approximately 1.3 milliamps and approximately 2.0 milliamps.
4. Pulse Width: between approximately 10 microseconds and approximately 5000 microseconds, such as between approximately 100 microseconds and approximately 1000 microseconds, or between approximately 20 microseconds and approximately 450 microseconds.

Accordingly, in some examples, stimulation generator 202 generates electrical stimulation signals in accordance with the electrical stimulation parameters noted above. Other ranges of therapy parameter values may also be useful, and may depend on the target stimulation site within patient 112. While stimulation pulses are described, stimulation signals may be of any form, such as continuous-time signals (e.g., sine waves) or the like. Stimulation signals configured to elicit ECAPs or other evoked physiological signals (e.g., resonant response) may be similar or different from the above parameter value ranges.

Processor 210 may include fixed function processing circuitry and/or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 210 herein may be embodied as firmware, hardware, software or any combination thereof. Processor 210 may control stimulation generator 202 according to therapy programs 214 stored in memory 211 to apply particular stimulation parameter values specified by one or more of programs, such as waveform pattern, voltage amplitude or current amplitude, pulse width, or pulse rate.

In the example shown in FIG. 2, the set of electrodes 116 includes electrodes 116A, 116B, 116C, and 116D, and the set of electrodes 118 includes electrodes 118A, 118B, 118C, and 118D. Processor 210 may control stimulation generator 202, which may include independently controllable current sources and sinks, to apply the stimulation signals to respective electrodes 116, 118. For example, processor 210 may control stimulation generator 202 to gate transistors on at the sources or sinks as desired. In this manner, stimulation generator 202 may be configured to selectively source or sink two or more electrodes to form an electrode combination/configuration for delivering electrical stimulation to the patient via the respective electrodes. Processor 210 may control one or more switches to couple or decouple sensing module 204 from electrodes 116, 118 to enable sensing from one or more electrodes and/or isolate sensing module 204 from delivered stimulation generated by stimulation generator 202 (e.g., during a blanking period to avoid recording stimulus artifact).

In other examples, IMD 106 may include a switch module (not shown) that may couple stimulation signals to selected conductors within leads 114, which, in turn, deliver the stimulation signals across selected electrodes 116, 118. The switch module may be a switch array, switch matrix, multiplexer, or any other type of switching module configured to selectively couple stimulation energy to selected electrodes 116, 118 and, in some examples, to selectively sense neurological brain signals with selected electrodes 116, 118. Hence, stimulation generator 202 may be coupled to electrodes 116, 118 via the switch module and conductors within leads 114. The switch module may be used for single channel or multi-channel stimulation generators.

Stimulation generator 202 may be a multi-channel stimulation generator with independent current sources and sinks as described above. In particular, stimulation generator 202 may be capable of delivering a single stimulation pulse, multiple stimulation pulses, or a continuous signal at a given time via a single electrode combination or multiple stimulation pulses at a given time via multiple electrode combinations. In some examples, however, stimulation generator 202 may be configured to deliver multiple channels on a time-interleaved basis. For example, stimulation generator 202 may comprise multiple voltage or current sources and sinks that are coupled to respective electrodes to drive the electrodes as cathodes or anodes. In this example, IMD 106 may not require the functionality of a switch module or time-interleaved multiplexing of stimulation via different electrodes.

Electrodes 116, 118 on respective leads 114 may be constructed of a variety of different designs. For example, one or both of leads 114 may include two or more electrodes at each longitudinal location along the length of the lead, such as multiple electrodes at different perimeter locations around the perimeter of the lead at each of the locations A, B, C, and D.

Although sensing module 204 may be incorporated into a common housing with stimulation generator 202 and processor 210 in FIG. 2, in other examples, sensing module 204 may be in a separate housing from IMD 106 and may communicate with processor 210 via wired or wireless communication techniques.

Sensor 212 may include one or more sensing elements that sense values of a respective patient parameter. For example, sensor 212 may include one or more accelerometers, optical sensors, chemical sensors, temperature sensors, pressure sensors, or any other types of sensors. Sensor 212 may output patient parameter values that may be used as feedback to control delivery of therapy. IMD 106 may include additional sensors within the housing of IMD 106 and/or coupled via one of leads 114 or other leads. In addition, IMD 106 may receive sensor signals wirelessly from remote sensors (e.g., wearable sensors) via telemetry module 208, for example. In some examples, one or more of these remote sensors may be external to patient (e.g., carried on the external surface of the skin, attached to clothing, or otherwise positioned external to the patient). For example, IMD 106 may determine from these one or more additional sensors the brain state (or disease state or symptom state) of the patient and sense signals for determining electrode movement during a brain state of lower fluctuation or lower noise to improve signal detection. In other examples, IMD 106 may employ an inertial sensor to determine when the patient is at rest (e.g., lying down and/or sleeping) and sense signals for determining lead movement during a time of rest to reduce noise or other motion artifacts in the sensed signals. In some examples, IMD 106 may sense signals for determining lead movement in response to receiving an indication that the patient received a dose of medication or the patient has entered a physician appointment.

Telemetry module 208 supports wireless communication between IMD 106 and an external programmer 104 or another computing device under the control of processor 210. Processor 210 of IMD 106 may receive, as updates to programs, values for various stimulation parameters such as magnitude and electrode combination/configuration, from programmer 104 via telemetry module 208. The updates to the therapy programs may be stored within therapy programs 214 portion of memory 211. In addition, processor 210 may control telemetry module 208 to transmit alerts or other information to programmer 104 that indicate a lead moved with respect to tissue. Telemetry module 208 in IMD 106, as well as telemetry modules in other devices and systems described herein, such as programmer 104, may accomplish communication by radiofrequency (RF) communication techniques. In addition, telemetry module 208 may communicate with external medical device programmer 104 via proximal inductive interaction of IMD 106 with programmer 104. Accordingly, telemetry module 208 may send information to external programmer 104 on a continuous basis, at periodic intervals, or upon request from IMD 106 or programmer 104.

Power source 220 delivers operating power to various components of IMD 106. Power source 220 may include a small rechargeable or non-rechargeable battery and a power generation circuit to produce the operating power. Recharging may be accomplished through proximal inductive interaction between an external charger and an inductive charging coil within IMD 220. In some examples, power requirements may be small enough to allow IMD 220 to utilize patient motion and implement a kinetic energy-scavenging device to trickle charge a rechargeable battery. In other examples, traditional batteries may be used for a limited period of time.

According to the techniques of the disclosure, processor 210 of IMD 106 delivers, electrodes 116, 118 interposed along leads 114, electrical stimulation therapy to patient 112. The DBS therapy is defined by one or more therapy programs 214 having one or more parameters stored within memory 211. For example, the one or more parameters include a current amplitude (for a current-controlled system) or a voltage amplitude (for a voltage-controlled system), a waveform pattern, a pulse rate or frequency, and a pulse width, or quantity of pulses per cycle. In examples where the electrical stimulation is delivered according to a "burst" of pulses, or a series of electrical pulses defined by an "on-time" and an "off-time," the one or more parameters may further define one or more of a number of pulses per burst, an on-time, and an off-time (e.g., as in cycling).

According to one or more techniques of the disclosure, processor 210 of IMD 106 receives MRI data of tissue of the patient that receives electrical stimulation via the electrodes 116, 118 of leads 114. The processor 210 may generate, based on the MRI data, stimulation temperature data representative of temperature changes in the tissue of the patient during the electrical stimulation. In some examples, the processor 210 may generate, based on the stimulation temperature data, a stimulation temperature map representative of the temperature values at different spatial locations within tissue of the patient (e.g., a two dimensional or three dimensional map). In some examples, the processor 210 may determine based on the temperature data, an orientation of the at least one electrode with respect to tissue of the patient.

In some examples, processor 210 of IMD 106 receives MRI data of tissue of the patient prior to or without electrical stimulation via the electrodes 116, 118 of leads 114. The processor 210 may generate, based on the MRI data, baseline temperature data representative of existing tissue temperature of the patient without electrical stimulation. This baseline temperature data may be indicative of the normal temperature detected by the MRI as a result of patient's temperature status with inactive stimulation (detectable by the T-map) and/or position of leads 114 during the MRI scan. In some examples, normal temperature may equal the body temperature of a patient at 37 degrees Centigrade. In some examples, the processor 210 may determine based on the baseline temperature data, a base temperature map. In some examples, the processor 210 may determine an orientation of the at least one electrode with respect to tissue of the patient based on comparing the baseline temperature map with the stimulation temperature map. In some examples, the processor 210 may determine if an electrode has moved based on comparing a first temperature map with a second temperature map, based on temperature data generated from MRI data, where the maps were generated for temperature data taken at two different time periods or instances. For example, since elevated temperatures may be associated with tissue adjacent an electrode delivering stimulation, the elevated temperatures identified at different anatomical positions may be indicating that the electrode(s) has moved, deviated, migrated, displaced, or re-oriented from the prior MRI scan.

In some examples, the electrode orientation may be determined based on the MRI temperature data and other sensed information from tissue. An example sensed information may be neurological signals sensed from the same tissue in the MRI temperature data or temperature map. For example, sensing module 204 may sense an electrical signal that is a neurological signal (e.g., a LFP signal) within the beta frequency band of brain 120 of patient 112. The signal within the beta frequency band of patient 112 may correlate to one or more symptoms of Parkinson's disease in patient 112. Generally speaking, neurological signals within the beta frequency band of patient 112 may be approximately proportional to the severity of the symptoms of patient 112. For example, as bradykinesia or rigidity induced by Parkinson's disease increases, one or more of electrodes 116, 118 detect an increase in the magnitude of neurological signals within the beta frequency band of patient 112. In this manner, the closest electrode combination to the origin of this neurological signal may be selected for therapy. When a lead rotates or shifts longitudinally, a different electrode combination may be best positioned to stimulate the tissue generating the neurological signal indicative of patient symptoms or of patient side-effects. Processor 210 may determine when this shift occurs with the electrodes and determines that the lead has moved. In some examples, processor 210 may receive stimulation MRI data, or MRI data in combination with characteristic values of the signals sensed by the electrode combinations, or any other information representative of the sensed electrical signals, such as, but not limited to, local field potential (LFP) data. In some examples, movement of the electrode detected by the LFP data may be correlated with the MRI data. In some examples, the MRI data may be re-done if the LFP data indicates movement of the electrode and the initial MRI data does not indicate movement. In some examples, the characteristic values of the signals sensed by the electrode combinations, or any other information representative of the sensed electrical signals, such as, but not limited to, local field potential (LFP) data may be used to confirm the MRI data. In some examples, the LFP data may be utilized to monitor movement of the electrode over time. In some examples, the LFP data may be utilized to confirm movement of the electrode determined by the MRI data. In one or more examples, the LFP data may trigger a request for additional MRI data, for example, if the LFP data indicates a potential movement of the electrode.

Processor 210 may automatically adjust the electrode combination for delivering therapy and/or other stimulation parameter values to compensate for the moved lead. Alternatively, processor 210 may transmit an alert to programmer 104 or other external device to indicate that updated stimulation parameters may be needed to continue efficacious therapy. For example, if the adjustments to electrode combinations and/or stimulation parameter values to compensate for the moved lead fall within respective ranges approved by the clinician, processor 210 may automatically adjust the electrode combination and/or other stimulation parameter values. If the adjustments to electrode combinations and/or stimulation parameter values to compensate for the moved lead do not fall within respective ranges approved by the clinician, processor 210 may communicate with programmer 104 to request approval or parameter values from a user.

Figure 3:
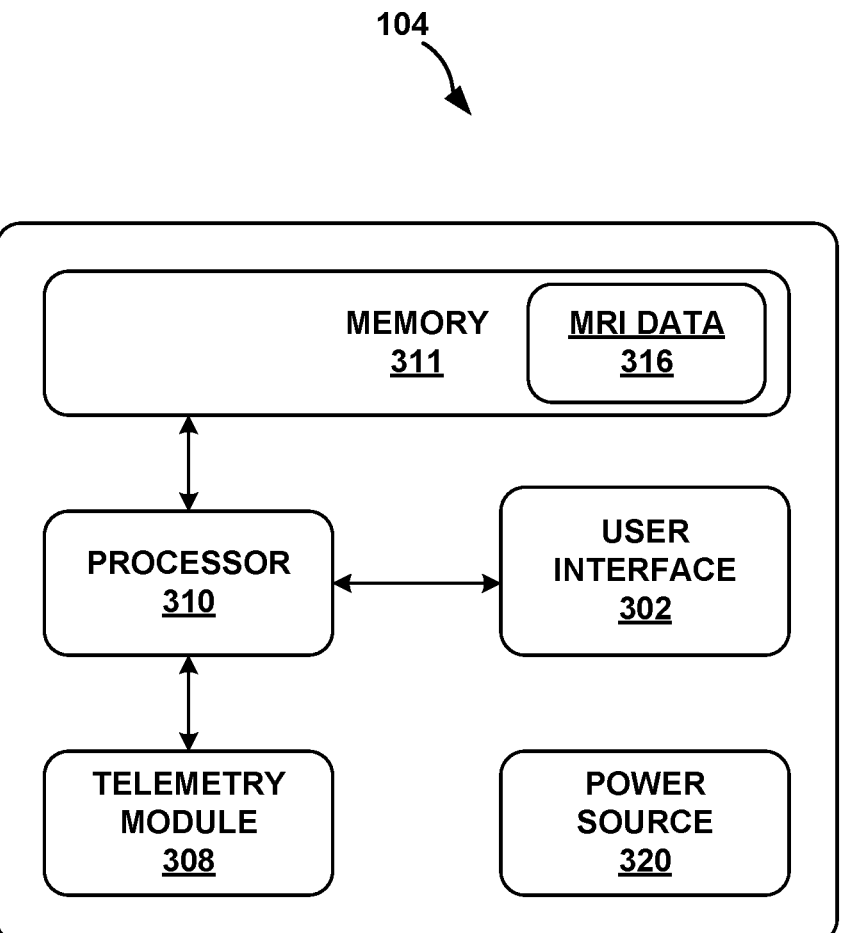
FIG. 3 is a block diagram of the external programmer of FIG. 1 for controlling delivery of DBS therapy according to an example of the techniques of the disclosure.

FIG. 3 is a block diagram of the external programmer 104 of FIG. 1 for determining electrode orientation in tissue and/or controlling delivery of DB S therapy according to an example of the techniques of the disclosure. Although programmer 104 may generally be described as a hand-held device, programmer 104 may be a larger portable device or a more stationary device. In some examples, programmer 104 may be referred to as a tablet computing device. In addition, in other examples, programmer 104 may be included as part of a bed-side monitor, an external charging device or include the functionality of an external charging device. As illustrated in FIG. 3, programmer 104 may include a processor 310, memory 311, user interface 302, telemetry module 308, and power source 320. Memory 311 may store instructions that, when executed by processor 310, cause processor 310 and external programmer 104 to provide the functionality ascribed to external programmer 104 throughout this disclosure. Each of these components, or modules, may include electrical circuitry that is configured to perform some or all of the functionality described herein. For example, processor 310 may include processing circuitry configured to perform the processes discussed with respect to processor 310.

In general, programmer 104 comprises any suitable arrangement of hardware, alone or in combination with software and/or firmware, to perform the techniques attributed to programmer 104, and processor 310, user interface 302, and telemetry module 308 of programmer 104. In various examples, programmer 104 may include one or more processors, which may include fixed function processing circuitry and/or programmable processing circuitry, as formed by, for example, one or more microprocessors, DSPs, ASICs, FPGAs, or any other equivalent integrated or discrete logic circuitry, as well as any combinations of such components. Programmer 104 also, in various examples, may include a memory 311, such as RAM, ROM, PROM, EPROM, EEPROM, flash memory, a hard disk, a CD-ROM, a DVD comprising executable instructions for causing the one or more processors to perform the actions attributed to them. Moreover, although processor 310 and telemetry module 308 are described as separate modules, in some examples, processor 310 and telemetry module 308 may be functionally integrated with one another. In some examples, processor 310 and telemetry module 308 correspond to individual hardware units, such as ASICs, DSPs, FPGAs, or other hardware units.

Memory 311 (e.g., a storage device) may store instructions that, when executed by processor 310, cause processor 310 and programmer 104 to provide the functionality ascribed to programmer 104 throughout this disclosure. For example, memory 311 may include instructions that cause processor 310 to obtain a parameter set from memory, select a spatial electrode movement pattern, provide an interface that recommends or otherwise facilitates parameter value selection, or receive a user input and send a corresponding command to IMD 106, or instructions for any other functionality. In addition, memory 311 may include a plurality of programs, where each program includes a parameter set that defines stimulation therapy.

According to one or more techniques of the disclosure, processor 310 of programmer 104 may receive MRI data of tissue of the patient that receives electrical stimulation via the electrodes 116, 118 of leads 114. Processor 310 may perform the same or similar functions as described with respect to processor 210 of IMD 106. Processor 310 may generate, based on the MRI data, stimulation temperature data representative of temperature changes in the tissue of the patient during the electrical stimulation. In some examples, the processor 310 may generate, based on the stimulation temperature data, a stimulation temperature map (See e.g., FIG. 7). In some examples, the processor 210 may determine based on the temperature data, an orientation of the at least one electrode with respect to tissue of the patient.

In some examples, processor 310 of IMD 106 receives MRI data of tissue of the patient prior to or without electrical stimulation via the electrodes 116, 118 of leads 114. The processor 310 may generate, based on the MRI data, baseline temperature data representative of normal temperature in the tissue of the patient without electrical stimulation. In some examples, the processor 310 may determine based on the baseline temperature data, a baseline temperature map (See e.g., FIG. 6). In some examples, the processor 310 may determine an orientation of the at least one electrode with respect to tissue of the patient based on comparing the baseline temperature map with the stimulation temperature map. For example, processor 310 may determine that relatively higher temperatures adjacent the lead corresponding to electrode locations when compared to corresponding lower temperatures adjacent the lead. In some examples, the processor 310 may determine if an electrode has moved based on comparing a first temperature map with a second temperature map, based on temperature data generated from MRI data, where the maps were generated for temperature data taken at two different time periods or instances. For example, if elevated temperatures in the temperature maps are different adjacent the lead, processor 310 may determine that the electrodes have moved with respect to the tissue. In one example, processor 310 may generate a gradient temperature map based on the first and second temperature maps. Processor 310 may then determine the direction of the change in temperature according to the gradient temperature map and correlate the electrode orientation to the direction of the change in temperature (e.g., an increase in temperature).

User interface 302 may include a button or keypad, lights, a speaker for voice commands, a display, such as a liquid crystal (LCD), light-emitting diode (LED), or organic light-emitting diode (OLED). In some examples the display may be a touch screen. User interface 302 may be configured to display any information related to the delivery of stimulation therapy, identified patient behaviors, sensed patient signal or parameter values, patient behavior criteria, or any other such information. User interface 302 may also receive user input via user interface 302. The input may be, for example, in the form of pressing a button on a keypad or selecting an icon from a touch screen or a gesture.

Telemetry module 308 may support wireless communication between IMD 106 and programmer 104 under the control of processor 310. Telemetry module 308 may also be configured to communicate with another computing device via wireless communication techniques, or direct communication through a wired connection. In some examples, telemetry module 308 provides wireless communication via an RF or proximal inductive medium. In some examples, telemetry module 308 includes an antenna, which may take on a variety of forms, such as an internal or external antenna. In some examples, IMD 106 and/or programmer 104 may communicate with remote servers via one or more cloud-services in order to deliver and/or receive information between a clinic and/or programmer.

Examples of local wireless communication techniques that may be employed to facilitate communication between programmer 104 and IMD 106 include RF communication according to the 802.11 or Bluetooth specification sets or other standard or proprietary telemetry protocols. In this manner, other external devices may be capable of communicating with programmer 104 without needing to establish a secure wireless connection. As described herein, telemetry module 308 may be configured to transmit a spatial electrode movement pattern or other stimulation parameter values to IMD 106 for delivery of stimulation therapy.

According to the techniques of the disclosure, in some examples, processor 310 of external programmer 104 defines the parameters of a homeostatic therapeutic window, stored in memory 311, for delivering DBS to patient 112. In one example, processor 311 of external programmer 104, via telemetry module 308, issues commands to IMD 106 causing IMD 106 to deliver electrical stimulation therapy via electrodes 116, 118 via leads 114.

Figures 4A, 4B:
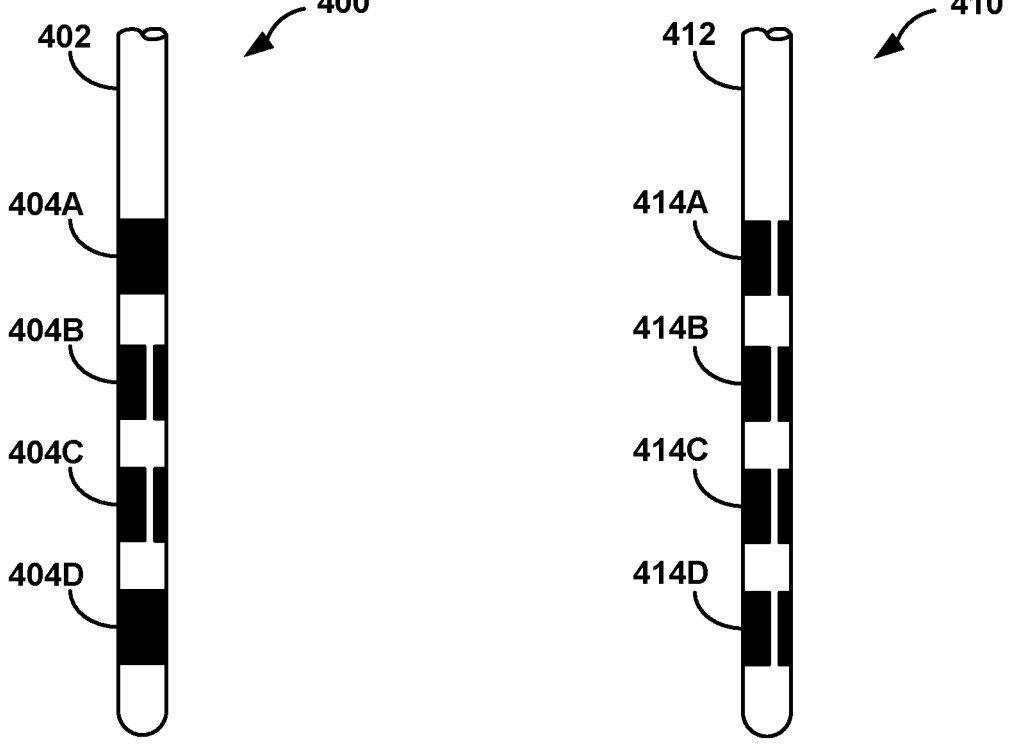
FIGS. 4A and 4B are conceptual diagrams of example leads with respective electrodes carried by the lead.

FIGS. 4A and 4B are conceptual diagrams of example leads 400 and 410, respectively, with respective electrodes carried by the lead. As shown in FIGS. 4A and 4B, leads 400 and 410 are embodiments of leads 114 shown in FIG. 1. As shown in FIG. 4A, lead 400 includes four electrode levels 404 (includes levels 404A-404D) mounted at various lengths of lead housing 402 (along the lead shaft). Lead 400 is inserted into through cranium 122 to a target position within brain 18.

Lead 400 is implanted within brain 120 at a location determined by the clinician to be near an anatomical region to be stimulated. Electrode levels 404A, 404B, 404C, and 404D may be equally spaced along the axial length of lead housing 402 at different axial positions. Each electrode level 404 may have one, two, three, or more electrodes located at different angular positions around the circumference (e.g., around the perimeter or the lead shaft) of lead housing 402. As shown in FIG. 4A, electrode level 404A and 404D include a single respective ring electrode, and electrode levels 404B and 404C each include three electrodes at different circumferential positions. This electrode pattern may be referred to as a 1-3-3-1 lead in reference to the number of electrodes from the proximal end to the distal end of lead 400. Electrodes of one circumferential location may be lined up on an axis parallel to the longitudinal axis of lead 400. Alternatively, electrodes of different electrode levels may be staggered around the circumference of lead housing 402. In addition, lead 400 or 410 may include asymmetrical electrode locations around the circumference, or perimeter, of each lead or electrodes of the same level that have different sizes. These electrodes may include semi-circular electrodes that may or may not be circumferentially aligned between electrode levels.

Lead housing 402 may include a radiopaque stripe (not shown) along the outside of the lead housing. The radiopaque stripe corresponds to a certain circumferential location that allows lead 400 to the imaged when implanted in patient 112. Using the images of patient 112, the clinician can use the radiopaque stripe as a marker for the exact orientation of lead 400 within the brain of patient 112. Orientation of lead 400 may be needed to easily program the stimulation parameters by generating the correct electrode configuration to match the stimulation field defined by the clinician. In other embodiments, a marking mechanism other than a radiopaque stripe may be used to identify the orientation of lead 400. These marking mechanisms may include something similar to a tab, detent, or other structure on the outside of lead housing 402. In some embodiments, the clinician may note the position of markings along a lead wire during implantation to determine the orientation of lead 400 within patient 112. In some examples, programmer 104 may update the orientation of lead 400 in visualizations based on the movement of lead 400 from sensed signals.

FIG. 4B illustrates lead 410 that includes multiple electrodes at different respective circumferential positions at each of levels 414A-414D. Similar to lead 400, lead 410 is inserted through a burr hole in cranium 122 to a target location within brain 120. Lead 410 includes lead housing 412. Four electrode levels 414 (414A-414D) are located at the distal end of lead 410. Each electrode level 414 is evenly spaced from the adjacent electrode level and includes two or more electrodes. In one embodiment, each electrode level 414 includes three, four, or more electrodes distributed around the circumference of lead housing 412. Therefore, lead 410 includes 414 electrodes in a preferred embodiment. Each electrode may be substantially rectangular in shape. Alternatively, the individual electrodes may have alternative shapes, e.g., circular, oval, triangular, rounded rectangles, or the like.

In alternative embodiments, electrode levels 404 or 414 are not evenly spaced along the longitudinal axis of the respective leads 400 and 410. For example, electrode levels 404C and 404D may be spaced approximately 3 millimeters (mm) apart while electrodes 404A and 404B are 10 mm apart. Variable spaced electrode levels may be useful in reaching target anatomical regions deep within brain 120 while avoiding potentially undesirable anatomical regions. Further, the electrodes disposed at adjacent levels need not be aligned in the direction as the longitudinal axis of the lead, and instead may be oriented diagonally with respect to the longitudinal axis.

Leads 400 and 410 are substantially rigid to prevent the implanted lead from varying from the expected lead shape. Leads 400 or 410 may be substantially cylindrical in shape. In other embodiments, leads 400 or 410 may be shaped differently than a cylinder. For example, the leads may include one or more curves to reach target anatomical regions of brain 120. In some embodiments, leads 400 or 410 may be similar to a flat paddle lead or a conformable lead shaped for patient 112. Also, in other embodiments, leads 400 and 410 may be any of a variety of different polygonal cross sections (e.g., triangle, square, rectangle, octagonal, etc.) taken transverse to the longitudinal axis of the lead.

As shown in the example of a passive tip lead 400, the plurality of electrodes of lead 400 includes a first set of three electrodes disposed at different respective positions around the longitudinal axis of the lead and at a first longitudinal position along the lead (e.g., electrode level 404B), a second set of three electrodes disposed at a second longitudinal position along the lead different than the first longitudinal position (e.g., electrode level 404C), and at least one ring electrode disposed at a third longitudinal position along the lead different than the first longitudinal position and the second longitudinal position (e.g., electrode level 404A and/or electrode level 404D). In some examples, electrode level 404B may have at least two electrodes disposed at different positions around a perimeter of the lead. In some examples, at least two electrodes are disposed at different axial positions along the lead (404B, 404C). In some examples, electrode level 404D may be a bullet/active tip or cone shaped electrode that covers the distal end of lead 402.

FIGS. 5A-5D are transverse cross-sections of example stimulation leads having one or more electrodes around the circumference of the lead. As shown in FIGS. 5A-5D, one electrode level, such as one of electrode levels 404 and 414 of leads 400 and 410, are illustrated to show electrode placement around the perimeter, or around the longitudinal axis or shaft, of the lead. FIG. 5A shows electrode level 500 that includes circumferential electrode 502. Circumferential electrode 502 encircles the entire circumference of electrode level 500 and may be referred to as a ring or omnidirectional electrode in some examples. Circumferential electrode 502 may be utilized as a cathode or anode or for sensing/recording as configured by the user interface.

FIG. 5B shows electrode level 510 which includes two electrodes 512 and 514. Each electrode 512 and 514 wraps approximately 170 degrees around the circumference of electrode level 510. Spaces of approximately 10 degrees are located between electrodes 512 and 514 to prevent inadvertent coupling of electrical current between the electrodes. Smaller or larger spaces between electrodes (e.g., between 10 degrees and 30 degrees) may be provided in other examples. Each electrode 512 and 514 may be programmed to act as an anode or cathode or for sensing/recording.

FIG. 5C shows electrode level 520 which includes three equally sized electrodes 522, 524 and 526. Each electrode 522, 524 and 526 encompass approximately 110 degrees of the circumference of electrode level 520. Similar to electrode level 510, spaces of approximately 10 degrees separate electrodes 522, 524 and 526. Smaller or larger spaces between electrodes (e.g., between 10 degrees and 30 degrees) may be provided in other examples. Electrodes 522, 524 and 526 may be independently programmed as an anode or cathode for stimulation or for sensing/recording.

FIG. 5D shows electrode level 530 which includes four electrodes 532, 534, 536 and 538. Each electrode 532, 534, 536 and 538 covers approximately 80 degrees of the circumference with approximately 10 degrees of insulation space between adjacent electrodes. Smaller or larger spaces between electrodes (e.g., between 10 degrees and 30 degrees) may be provided in other examples. In other embodiments, up to ten or more electrodes may be included within an electrode level. In alternative embodiments, consecutive electrode levels of lead 114 may include a variety of electrode levels 500, 510, 520, and 530. For example, lead 114 (or any other lead described herein) may include electrode levels that alternate between electrode levels 510 and 530 depicted in FIGS. 5B and 5D. In this manner, various stimulation field shapes may be produced within brain 120 of patient 112. Leads could have low- or high-resolution segmented electrode designs. Further the above-described sizes of electrodes within an electrode level are merely examples, and the invention is not limited to the example electrode sizes.

FIG. 6 is an axial view of an example temperature map 600 based on baseline temperature data representative of normal tissue temperature, inferred by processing circuitry. The baseline temperature data may be generated based on MRI data taken prior to or without electrical stimulation. FIG. 6 shows electrodes 606A, 606B of a lead with respect to tissue 602, where 606A, 606B represent two different segments of electrodes disposed on opposite sides of a lead in a plurality of plausible radial orientations. Anatomical directions such as anterior, posterior, medial, and lateral are shown with respect to the anatomy in this example. In addition, or alternatively, in-between directions such as anterio-lateral, anterio-medial, posterior-medial, and posterio-lateral may be provided. Other directions may be shown based on the orientation of the 2D or 3D anatomical view. The temperature map shows varying levels of temperature 610, 612, 614, 616 relative to the electrodes 606A and 606B, with area 616 being the warmest, area 612 being the second warmest, area 614 being the third warmest, and area 610 the coolest (e.g., at normal tissue temperature). Area 616 generally surrounds both electrodes 606A, 606B. Temperature differences between two or more of the areas may be within 2 degrees Centigrade. In some examples, temperature difference between two or more of the areas may be 0.8 to 1 degree Centigrade. In some examples, temperature difference between two or more of the areas may be 0.1 to 1.5 degrees Centigrade.

Figure 7:
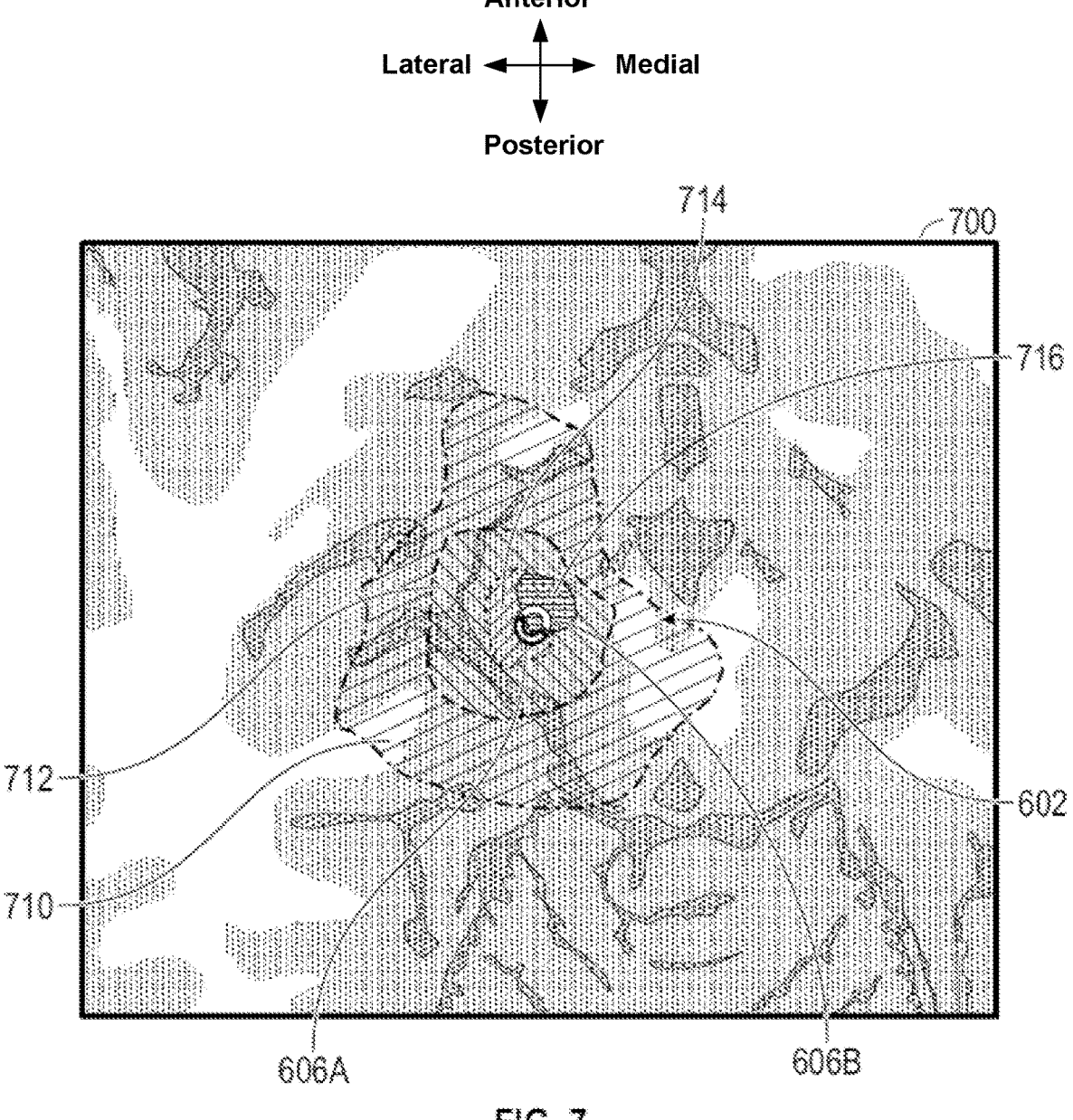
FIG. 7 is a temperature map of tissue with a lead placed within tissue.

FIG. 7 is an axial view of an example temperature map 700. When the tissue is stimulated by electrodes, the surrounding tissue raises in temperature, and the resulting temperature rise may be captured by MRI data. Heat is generated due to both Joule heating from the applied stimulation (e.g. when stimulation is applied for but not limited to five or fifteen minutes) and through increased metabolism rates caused by physiological shifts in neurons influenced by the stimulation. Although heating via electrical stimulation is described as one example, the system may generate heating in tissue via another mechanism such as via optional heating caused by delivered light energy, ultrasound heating, or any other mechanism that results in tissue heating. Anatomical directions such as anterior, posterior, medial, and lateral are shown with respect to the anatomy in this example. Temperature map 700 may be generated by processing circuitry, and may be based on the MRI temperature data representative of temperature changes in tissue. The temperature data may be generated based on MRI data taken during or after electrical stimulation of tissue. Similar to FIG. 6, FIG. 7 shows again a lead and electrodes 606A, 606B placed with respect to tissue 602, where 606A, 606B represent two different segments of electrodes disposed on opposite sides of a lead, and electrical stimulation has been applied to electrode 606B. The temperature map shows varying levels of temperature 710, 712, 714, 716, relative to the electrodes 606A and 606B, with area 716 being the warmest, area 714 being the second warmest, area 712 being the third warmest, and 710 the coolest (e.g., at normal tissue temperature). The relative warmest area 716 surrounds (or is skewed/biased in the direction of) only electrode 606B, and not 606A, indicating that electrode 606B is the electrode to which stimulation was applied. In some examples, the electrodes are identified based on the temperatures. Using this temperature map 700 and information that electrode 606B is the electrode providing electrical stimulation to the tissue, processing circuitry may determine orientation of the electrode 606B relative to the tissue. In some examples, processing circuitry may determine or infer the orientation of additional electrodes by applying stimulation to one or more additional electrodes, and developing another temperature map. In other examples, the processing circuitry may utilize stimulation and respective temperature increases associated with multiple electrodes in order to more precisely determine the electrode orientations than may be possible by only using a single electrode. In some examples, processing circuitry may determine orientation of two or more electrodes, and use the orientation of the two electrodes to identify or infer orientation of additional electrodes. In some examples, processing circuitry may determine orientation of two or more electrodes at different axial levels of the lead, and use the orientation of the two electrodes to identify or infer orientation of additional electrodes. In some examples, processing circuitry may determine orientation of two or more electrodes, where the temperature may be higher at a cathode compared to the anode. In some examples, processing circuitry may use anodes and/cathodes at a similar radial position however different axial positions (along the lead shaft). In some examples, processing circuitry may determine location, and may further determine or infer orientation of other electrodes for example by using known relative geometry of the electrodes. For example, processing circuitry may extrapolate other electrode locations because of the known electrode positions on the lead.

Figure 8:
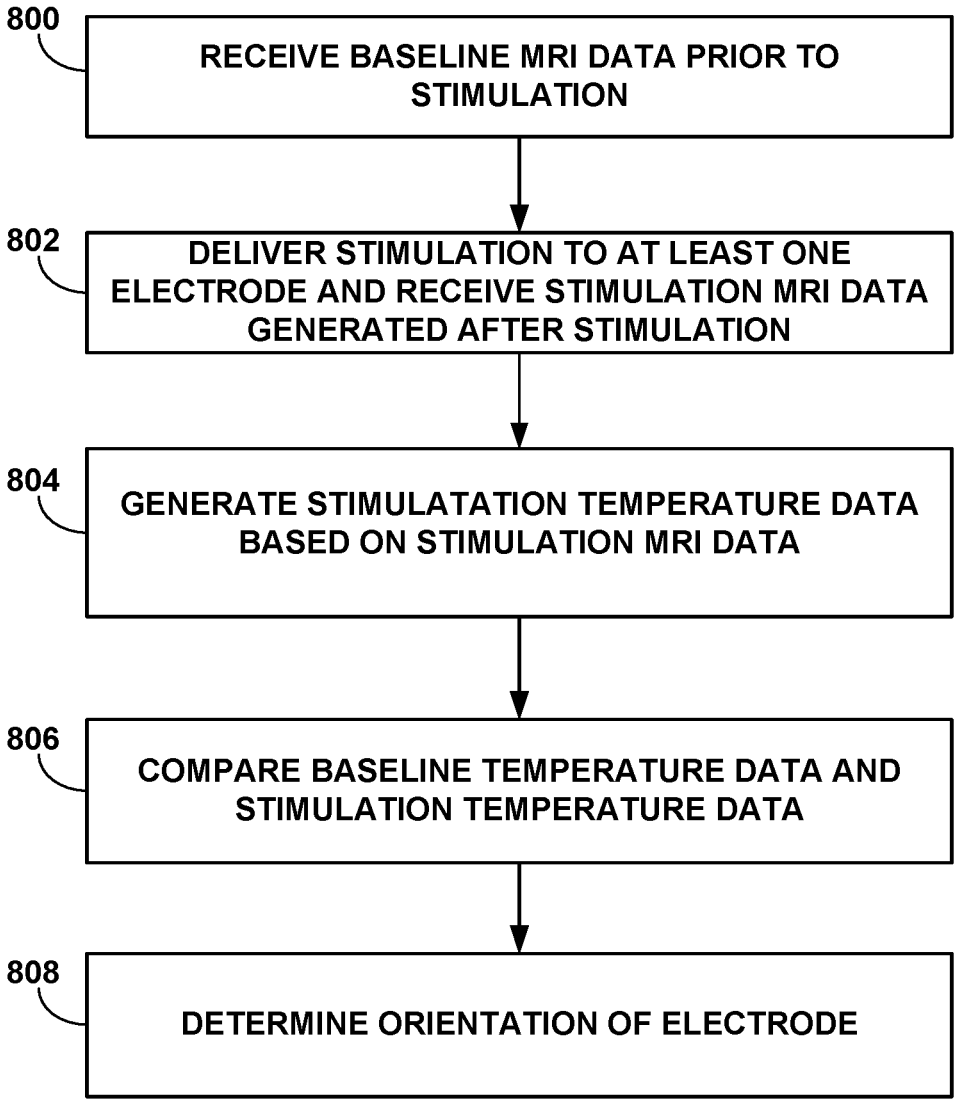
FIG. 8 is a flowchart illustrating an example technique for determining orientation of the electrode with respect to tissue.

FIG. 8 is a flowchart illustrating an example technique for determining orientation of a lead electrode with respect to tissue. The technique of FIG. 8 will be described with respect to processor 210 of IMD 106 in FIG. 2. However, other processors, devices, or combinations thereof, may perform the techniques of FIG. 8 in other examples.

As shown in the example of FIG. 8, processor 210 receives initial information such as baseline MRI data prior to stimulation for electrode combination, for example, at a first time (800). The initial information may be MRI data, or MRI data in combination with characteristic values of the signals sensed by the electrode combinations, or any other information representative of the sensed electrical signals. If processor 210 receives signal information, processor 210 may determine one or more characteristic values for the signal information for each electrode combination. Processor 210 may generate baseline temperature data from the MRI data, and may use the baseline temperature data representative of normal temperature in the tissue of the patient without electrical stimulation to generate a baseline temperature map based on the baseline temperature data.

Processor 210 may control stimulation to be delivered to at least one electrode, for example in bipolar mode where two or more electrodes on the same lead are part of the electrode combination by which stimulation is delivered to the patient. Although temperature profile by stimulation induced changes (and orientation) may be determined for as few as one electrode, electrical stimulation is delivered via at least two electrodes (e.g., between at least one anode and at least one cathode). In some examples, processor 210 may direct stimulation in unipolar mode by sending stimulation between an electrode on the lead and another reference electrode carried by the housing of IMD 106 or other return electrode more proximal on the lead such as near the skull. In some examples, differentiated stimulation may be delivered to two or more different electrodes that will result in correspondingly differentiated temperature changes. The differential temperature zones can also be used in the MRI temperature map to distinguish between different electrode segments on a lead.

In some examples, processor 210 receives stimulation MRI data generated during or immediately after stimulation or after a lockout period (e.g. approximately but not limited to five or fifteen minutes) (802). In some examples, the stimulation MRI data received by processor 210 may be generated during stimulation. If processor 210 receives signal information, processor 210 may determine one or more characteristic values for the signal information for each electrode combination. Processor 210 may generate stimulation temperature data from the stimulation MRI data (804). In some examples, processor 210 may use the temperature data representative of temperature changes in the tissue of the patient after electrical stimulation to generate a temperature map based on the temperature data. Processor 210 may compare baseline temperature data and stimulation temperature data (806). For example, processor 210 may compare the baseline temperature map with the stimulation temperature map. In comparing the baseline data and the stimulation data, processor 210 may determine an orientation of an electrode of the lead (808). For example, the stimulation temperature map may reveal a highest temperature near a particular electrode, where the high temperature near the electrode was not indicated in the baseline temperature map. In some examples, the stimulation temperature map may reveal a highest temperature near a particular electrode, where the high temperature near the electrode was also indicated in the base temperature map. The stimulation electrode is known to processor 210, and the high temperature area is indicated in the stimulation temperature map.

Using this information, since the stimulation electrode is known, processor 210 may determine the electrode orientation relative to the tissue. In some examples, processor 210 may determine the electrode orientation relative to the tissue with regards to one of the primary directions: anterior, posterior, medial or lateral. In some examples, processor 210 may determine the electrode orientation relative to the tissue with regards to one of the secondary directions: anterior-lateral, anterior-medial, posterior-medial or posterior-lateral.

In one or more examples, processor 210 may receive stimulation MRI data, or MRI data in combination with characteristic values of the signals sensed and/or recorded by the electrode combinations, or any other information representative of the sensed electrical signals, such as, but not limited to, local field potential (LFP) data. In some examples, the characteristic values of the signals sensed by the electrode combinations, or any other information representative of the sensed electrical signals, such as, but not limited to, local field potential (LFP) data may be used to confirm the MRI data. In some examples, the LFP data may be utilized to monitor movement of the electrode over time. In some examples, the LFP data may be utilized to confirm movement of the electrode determined by the MRI data. In one or more examples, the LFP data may trigger a request for additional MRI data, for example, if the LFP data indicates a potential movement of the electrode.

Figure 9:
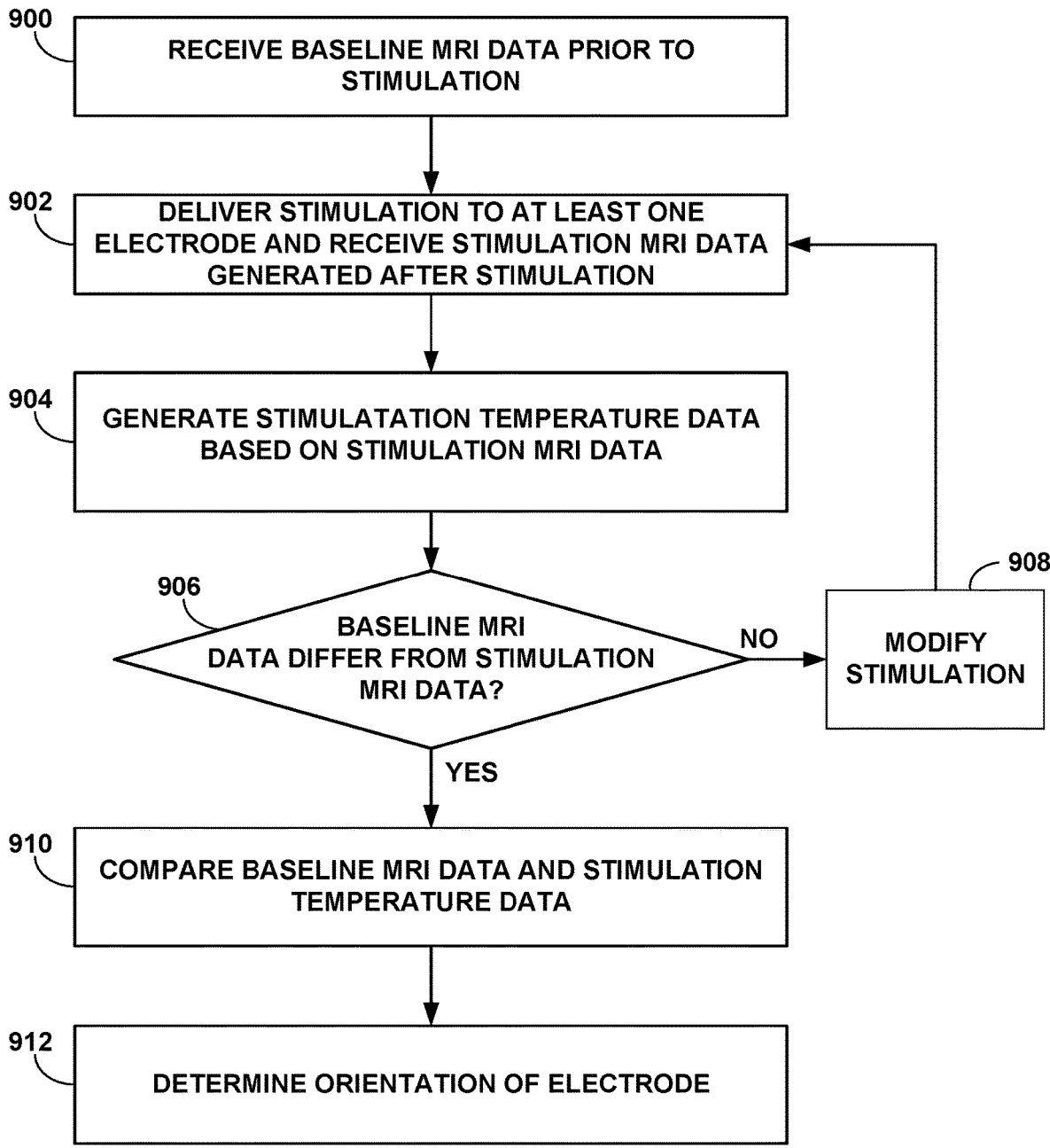
FIG. 9 is a flowchart illustrating an example technique for determining orientation of the electrode with respect to tissue.

FIG. 9 is a flowchart illustrating an example technique for determining orientation of a lead electrode with respect to tissue. The technique of FIG. 9 will be described with respect to processor 210 of IMD 106 in FIG. 2. However, other processors, devices, or combinations thereof, may perform the techniques of FIG. 8 in other examples.

As shown in the example of FIG. 9, processor 210 receives initial information such as baseline MRI data prior to stimulation for electrode combination, for example, at a first time (900). The initial information may be MRI data, or MRI data in combination with characteristic values of the signals sensed by the electrode combinations, or any other information representative of the sensed electrical signals. If processor 210 receives signal information, processor 210 may determine one or more characteristic values for the signal information for each electrode combination. Processor 210 may generate baseline temperature data from the MRI data, and may use the baseline temperature data representative of existing tissue temperature (e.g. normal body temperature) in the tissue of the patient without electrical stimulation to generate a baseline reference temperature map based on the baseline temperature data.

Processor 210 may direct stimulation to be delivered to at least one electrode with a certain set of stimulation parameters. The stimulation parameters may include a stimulation electrode combination for delivering stimulation to patient 112, waveform pattern, pulse frequency, pulse width, and a current or voltage amplitude of the pulses. In some examples, processor 210 may direct stimulation in unipolar mode by sending stimulation between an electrode on the lead and another reference electrode carried by the housing of IMD 106 or other return electrode more proximal on the lead such as near the skull.

In some examples, processor 210 receives stimulation MRI data generated after stimulation (902). In some examples, the stimulation MRI data received by processor 210 may be taken during stimulation. If processor 210 receives signal information, processor 210 may determine one or more characteristic values for the signal information for each electrode combination. Processor 210 may generate stimulation temperature data from the stimulation MRI data (904). In some examples, processor 210 may use the temperature data representative of temperature changes in the tissue of the patient after electrical stimulation to generate a temperature map based on the temperature data. Processor 210 may compare baseline temperature data and stimulation temperature data (906) and determine whether the baseline MRI data differs from the stimulation MRI data. For example, processor 210 may compare the baseline temperature map with the stimulation temperature map. When determining that the baseline MRI data and the stimulation MRI data are the same or different between different times, processor 210 may use a tolerance or deviation threshold. The tolerance or deviation threshold may be a percentage of previous values.

If processor 210 determines that there is no difference or minimal difference between the baseline MRI data and the stimulation MRI data ("NO" branch of block 906), then processor 210 modifies stimulation parameters (908) and continues to control the delivery of stimulation to the electrode, and receive MRI data taken after stimulation (902). For example, processor 210 may increase amplitude of the stimulation delivered via the electrode, where the amplitude may be increased by a predetermined amount. This increase in amplitude and/or change to other stimulation parameters may be performed to increase the intensity of the electrical stimulation to induce controlled detectable temperature changes, that increases temperature in the tissue adjacent the one or more electrodes.

If processor 210 determines that there is a difference between baseline MRI data and the stimulation MRI data from sensed signals at different times ("YES" branch of block 906), processor 210 then compares baseline MRI data and the stimulation MRI data (910). The processor 210 then determines an orientation of the electrode with respect to surrounding tissue as described herein (912).

For example, to determine an orientation of an electrode of the lead (910), processor 210 may compare the baseline reference temperature map with the stimulation temperature map. For example, the stimulation temperature map may reveal a relatively higher temperature near a particular electrode at a particular location in the tissue, where the high temperature near the electrode was not indicated in the baseline reference temperature map. In some examples, the stimulation temperature map may reveal a highest temperature near a particular electrode, where the high temperature near the electrode was also indicated in the base temperature map. The stimulation electrode is known to processor 210, and the high temperature area is indicated in the stimulation temperature map. Using this information, since the stimulation electrode is known, processor 210 may determine the electrode orientation relative to the tissue (in one of the primary or secondary directions).

In one or more examples, processor 210 may receive stimulation MRI data, or MRI data in combination with characteristic values of the signals sensed by the electrode combinations, or any other information representative of the sensed electrical signals, such as, but not limited to, local field potential (LFP) data. In some examples, the characteristic values of the signals sensed by the electrode combinations, or any other information representative of the sensed electrical signals, such as, but not limited to, local field potential (LFP) data may be used to confirm the MRI data. In some examples, the LFP data may be utilized to monitor movement of the electrode over time. In some examples, the LFP data may be utilized to confirm movement of the electrode determined by the MRI data. In one or more examples, the LFP data may trigger a request for additional MRI data, for example, if the LFP data indicates a potential movement of the electrode. In some examples, LFP may be sensed without and with stimulation and compared with the corresponding MRI data without and with stimulation, for example to create a baseline reference data or determine if the electrode has moved.

Example 1: A method includes receiving, by a processing circuitry, magnetic resonance imaging (MRI) data of tissue of a patient that received electrical stimulation via at least one electrode of a plurality of electrodes disposed in the patient; generating, based on the MRI data, stimulation temperature change data representative of temperature changes in the tissue of the patient during the electrical stimulation; and determining, by the processing circuitry and based on the temperature data, an orientation of the at least one electrode with respect to the tissue of the patient.

Example 2: The method of example 1, wherein the tissue comprises brain tissue of the patient.

Example 3: The method of any of examples 1 or 2, wherein the at least one electrode comprises at least two electrodes disposed at different positions around a perimeter (or shaft) of an implanted lead.

Example 4: The method of any of examples 1 through 3, wherein the at least one electrode comprises at least two electrodes disposed at different axial positions along an implanted lead in the patient.

Example 5: The method of example 4, wherein the at least two electrodes disposed at different axial positions along the lead are also disposed at a same circumferential position around a perimeter of the implanted lead.

Example 6: The method of any of examples 1 through 5, wherein delivering stimulation comprises delivering unipolar stimulation.

Example 7: The method of any of examples 1 through 6, further comprising receiving MRI data of tissue of the patient without stimulation, generating, based on the MRI data, baseline temperature data representative of normal temperature in the tissue of the patient without electrical stimulation.

Example 8: The method of example 7, wherein the at least one electrode comprises a plurality of electrodes, wherein the method further comprises: comparing the stimulation temperature data with the baseline temperature data; and identifying one electrode of the plurality of electrodes corresponding to a change in temperature (e.g., an increase in temperature) during electrical stimulation, wherein determining the orientation of the one electrode with respect to the tissue of the patient comprises determining, based on the identified one electrode, the orientation of the at least one electrode with respect to the tissue.

Example 9: The method of example 8, further comprising generating a baseline temperature map from the baseline temperature data and generating a stimulation temperature map from the stimulation temperature data, and identifying an orientation of one electrode of the plurality of electrodes based on comparing the baseline temperature map with the stimulation temperature map.

Example 10: The method of any of examples 1 through 9, further comprising receiving local field potential (LFP) data generated at a same time the MRI data was generated, wherein determining the orientation of the at least one electrode with respect to the tissue of the patient comprises determining, based on the temperature data and the LFP data the orientation of the electrode with respect to the tissue of the patient.

Example 11: A system includes processing circuitry configured to: receive magnetic resonance imaging (MRI) data of tissue of a patient that received electrical stimulation via at least one electrode of a plurality of electrodes disposed in the patient; generate, based on the MRI data, stimulation temperature data representative of temperature changes in tissue of the patient during electrical stimulation; and determine, by the processing circuitry and based on the temperature data, an orientation of the at least one electrode with respect to the tissue of the patient.

Example 12: The system of example 11, wherein the tissue comprises brain tissue of the patient.

Example 13: The system of any of examples 11 and 12, wherein the at least one electrode comprises at least two electrodes disposed at different positions around a perimeter of an implanted lead.

Example 14: The system of any of examples 11 through 13, wherein the at least one electrode comprises at least two electrodes disposed at different axial positions along an implanted lead in the patient.

Example 15: The system of example 14, wherein the at least two electrodes disposed at different axial positions along the lead are also disposed at a same circumferential position around a perimeter of the implanted lead.

Example 16: The system of any of examples 11 through 15, wherein to deliver stimulation comprises to deliver unipolar stimulation.

Example 17: The system of any of examples 11 through 16, wherein the processing circuitry is further configured to receive MRI data of tissue of the patient without stimulation, generate, based on the MRI data, baseline temperature data representative of normal temperature in the tissue of the patient without electrical stimulation, and generate a baseline temperature map based on the baseline temperature data.

Example 18: The system of example 17, wherein the at least one electrode comprises a plurality of electrodes, wherein the processor is further configured to: generate a stimulation temperature map from the stimulation temperature data; compare the stimulation temperature map with the baseline temperature map; and identify one electrode of the plurality of electrodes corresponding to a temperature change during electrical stimulation, wherein to determine the orientation of the one electrode with respect to the tissue of the patient comprises to determine, based on the identified one electrode, the orientation of the at least one electrode with respect to the tissue.

Example 19: The system of any of examples 11 through 18, wherein the processing circuitry is further configured to receive local field potential (LFP) data generated at a same time the MRI data was generated, wherein determining the orientation of the at least one electrode with respect to the tissue of the patient comprises determining, based on the temperature data and the LFP data the orientation of the electrode with respect to the tissue of the patient.

Example 20: A computer-readable storage medium includes receive MRI data of tissue of a patient that received electrical stimulation via at least one electrode disposed in the patient; generate, based on the MRI data, stimulation temperature data representative of temperature changes in tissue of the patient during stimulation; and determine, by the processing circuitry and based on the temperature data, an orientation of the at least one electrode with respect to the tissue of the patient.

The techniques described in this disclosure may be implemented, at least in part, in hardware, software, firmware or any combination thereof. For example, various aspects of the described techniques may be implemented within one or more processors, such as fixed function processing circuitry and/or programmable processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a DVD, a floppy disk, a cassette, magnetic media, optical media, or other computer readable media.

Various examples have been described. These and other examples are within the scope of the following claims.

What is claimed is:

1. A method comprising:
receiving, by processing circuitry, magnetic resonance imaging (MRI) data of tissue of a patient that received electrical stimulation via at least one electrode of a plurality of electrodes disposed in the patient;
generating, based on the MRI data, stimulation temperature data representative of temperature changes in the tissue of the patient during the electrical stimulation; and
determining, by the processing circuitry and based on the temperature data and an anatomical position of the tissue, an orientation of the at least one electrode with respect to the tissue of the patient.

2. The method of claim 1, wherein the tissue comprises brain tissue of the patient.

3. The method of claim 1, wherein the at least one electrode comprises at least two electrodes disposed at different positions around a perimeter of an implanted lead.

4. The method of claim 1, wherein the at least one electrode comprises at least two electrodes disposed at different axial positions along an implanted lead in the patient.

5. The method of claim 4, wherein the at least two electrodes disposed at different axial positions along the lead are also disposed at a same circumferential position around a perimeter of the implanted lead.

6. The method of claim 1, wherein delivering stimulation comprises delivering unipolar stimulation.

7. The method of claim 1, further comprising receiving MRI data of tissue of the patient without stimulation, generating, based on the MRI data, baseline temperature data representative of normal temperature in the tissue of the patient without electrical stimulation.

8. The method of claim 7, wherein the at least one electrode comprises a plurality of electrodes, wherein the method further comprises:
comparing the stimulation temperature data with the baseline temperature data; and
identifying one electrode of the plurality of electrodes corresponding to a temperature change during electrical stimulation, wherein determining the orientation of the one electrode with respect to the tissue of the patient comprises determining, based on the identified one electrode, the orientation of the at least one other electrode with respect to the tissue.

9. The method of claim 8, further comprising generating a baseline temperature map from the baseline temperature data and generating a stimulation temperature map from the stimulation temperature data, and identifying an orientation of one electrode of the plurality of electrodes based on comparing the baseline temperature map with the stimulation temperature map.

10. The method of claim 1, further comprising receiving local field potential (LFP) data generated at a same time the MRI data was generated, wherein determining the orientation of the at least one electrode with respect to the tissue of the patient comprises determining, based on the temperature data and the LFP data the orientation of the electrode with respect to the tissue of the patient.

11. A system comprising:
processing circuitry configured to:
receive magnetic resonance imaging (MRI) data of tissue of a patient that received electrical stimulation via at least one electrode of a plurality of electrodes disposed in the patient;
generate, based on the MRI data, stimulation temperature data representative of temperature changes in tissue of the patient during electrical stimulation; and
determine, by the processing circuitry and based on the temperature data and an anatomical position of the tissue, an orientation of the at least one electrode with respect to the tissue of the patient.

12. The system of claim 11, wherein the tissue comprises brain tissue of the patient.

13. The system of claim 11, wherein the at least one electrode comprises at least two electrodes disposed at different positions around a perimeter of an implanted lead.

14. The system of claim 11, wherein the at least one electrode comprises at least two electrodes disposed at different axial positions along an implanted lead in the patient.

15. The system of claim 14, wherein the at least two electrodes disposed at different axial positions along the lead are also disposed at a same circumferential position around a perimeter of the implanted lead.

16. The system of claim 11, wherein to deliver stimulation comprises to deliver unipolar stimulation.

17. The system of claim 11, wherein the processing circuitry is further configured to receive MRI data of tissue of the patient without stimulation, generate, based on the MRI data, baseline temperature data representative of normal existing temperature in the tissue of the patient without electrical stimulation, and generate a baseline temperature map based on the baseline temperature data.

18. The system of claim 17, wherein the at least one electrode comprises a plurality of electrodes, wherein the processor is further configured to:

generate a stimulation temperature map from the stimulation temperature data;

compare the stimulation temperature map with the baseline temperature map; and identify one electrode of the plurality of electrodes corresponding to a temperature change during electrical stimulation, wherein to determine the orientation of the one electrode with respect to the tissue of the patient comprises to determine, based on the identified one electrode, the orientation of the at least one other electrode with respect to the tissue.

19. The system of claim 11, wherein the processing circuitry is further configured to receive local field potential (LFP) data generated at a same time the MRI data was generated, wherein determining the orientation of the at least one electrode with respect to the tissue of the patient comprises determining, based on the temperature data and the LFP data the orientation of the electrode with respect to the tissue of the patient.

20. A non-transitory computer-readable storage medium comprising instructions that, when executed, cause a processor to:

receive MRI data of tissue of a patient that received electrical stimulation via at least one electrode disposed in the patient;

generate, based on the MRI data, stimulation temperature data representative of temperature changes in tissue of the patient during stimulation; and determine, by the processing circuitry and based on the temperature data and an anatomical position of the tissue, an orientation of the at least one electrode with respect to the tissue of the patient.

* * * * *